(12) United States Patent
Robichaud et al.

(10) Patent No.: US 9,737,406 B2
(45) Date of Patent: Aug. 22, 2017

(54) ANATOMICALLY ADAPTED ORTHOPEDIC IMPLANT AND METHOD OF MANUFACTURING SAME

(71) Applicant: LABORATOIRES BODYCAD INC., Québec (CA)

(72) Inventors: Jean Robichaud, Quebec (CA); Marc Bédard, Pont-Rouge (CA); Geoffroy Rivet-Sabourin, Stoneham (CA)

(73) Assignee: LABORATORIES BODYCAD INC., Québec (CA)

(*) Notice: Subject to any disclaimer, the term of this patent is extended or adjusted under 35 U.S.C. 154(b) by 0 days.

(21) Appl. No.: 14/752,550

(22) Filed: Jun. 26, 2015

(65) Prior Publication Data
US 2015/0297350 A1    Oct. 22, 2015

Related U.S. Application Data

(63) Continuation-in-part of application No. PCT/CA2014/050797, filed on Aug. 20, 2014.
(Continued)

(51) Int. Cl.
*A61F 2/38* (2006.01)
*A61F 2/30* (2006.01)

(52) U.S. Cl.
CPC .......... *A61F 2/30942* (2013.01); *A61F 2/389* (2013.01); *A61F 2/3859* (2013.01); *A61F 2002/305* (2013.01); *A61F 2002/30331* (2013.01); *A61F 2002/30387* (2013.01); *A61F 2002/30578* (2013.01); *A61F 2002/30841* (2013.01); *A61F 2002/3895* (2013.01)

(58) Field of Classification Search
CPC ..... A61F 2/38; A61F 2/389; A61F 2002/3895
USPC .................. 623/20.32, 20.33, 20.3
See application file for complete search history.

(56) References Cited

U.S. PATENT DOCUMENTS 5,092,895 A * 3/1992 Albrektsson .......... A61F 2/3868
                                                      623/20.3
5,871,541 A * 2/1999 Gerber .................. A61F 2/3877
                                                     623/20.29
(Continued)

FOREIGN PATENT DOCUMENTS

| AU | 2007202573 | 6/2007 |
| AU | 2011203237 | 7/2011 |

(Continued)

OTHER PUBLICATIONS

European Search Report for Application No. EP 14837657, dated Mar. 16, 2017.

*Primary Examiner* — Alvin Stewart
(74) *Attorney, Agent, or Firm* — Marshall, Gerstein & Borun LLP

(57) ABSTRACT

An orthopedic implant to cover at least partially a surface of a bone of a patient. The orthopedic implant comprises a body having at least one retaining section, a bone-facing surface, and an articular surface. The at least one retaining section is configured to retain the orthopedic implant on the surface of the patient's bone along at least one axis by covering a corresponding retaining surface thereof. The bone-facing surface of at least one of the at least one retaining section nestingly conforms to an unresected portion of the surface of the bone of the patient. A method for conceiving and implanting an orthopedic implant is also provided.

19 Claims, 29 Drawing Sheets

Related U.S. Application Data

(60) Provisional application No. 61/868,236, filed on Aug. 21, 2013, provisional application No. 62/017,933, filed on Jun. 27, 2014.

(56) References Cited

U.S. PATENT DOCUMENTS

| | | | |
|---|---|---|---|
| 5,871,542 A * | 2/1999 | Goodfellow | A61F 2/3868 623/20.16 |
| 6,690,761 B2 | 2/2004 | Lang et al. | |
| 6,811,310 B2 | 11/2004 | Lang et al. | |
| 6,904,123 B2 | 6/2005 | Lang | |
| 7,033,397 B2 * | 4/2006 | Webster | A61F 2/3868 623/20.29 |
| 7,050,534 B2 | 5/2006 | Lang | |
| 7,058,159 B2 | 6/2006 | Lang et al. | |
| 7,105,027 B2 * | 9/2006 | Lipman | A61F 2/3868 623/20.29 |
| 7,120,225 B2 | 10/2006 | Lang et al. | |
| 7,245,697 B2 | 7/2007 | Lang | |
| 7,292,674 B2 | 11/2007 | Lang | |
| 7,357,057 B2 | 4/2008 | Chiang | |
| 7,379,529 B2 | 5/2008 | Lang | |
| 7,462,199 B2 * | 12/2008 | Justin | A61B 17/157 623/14.12 |
| 7,467,892 B2 | 12/2008 | Lang et al. | |
| 7,468,075 B2 | 12/2008 | Lang et al. | |
| 7,534,263 B2 | 5/2009 | Burdulis, Jr. et al. | |
| 7,545,964 B2 | 6/2009 | Lang et al. | |
| 7,580,504 B2 | 8/2009 | Lang et al. | |
| 7,618,451 B2 | 11/2009 | Berez et al. | |
| 7,634,119 B2 | 12/2009 | Tsougarakis et al. | |
| 7,660,453 B2 | 2/2010 | Lang | |
| 7,664,298 B2 | 2/2010 | Lang et al. | |
| 7,676,023 B2 | 3/2010 | Lang | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,840,247 B2 | 11/2010 | Liew et al. | |
| 7,967,868 B2 | 6/2011 | White et al. | |
| 7,981,158 B2 | 7/2011 | Fitz et al. | |
| 7,995,822 B2 | 8/2011 | Lang et al. | |
| 8,000,441 B2 | 8/2011 | Lang et al. | |
| 8,000,766 B2 | 8/2011 | Lang et al. | |
| 8,031,836 B2 | 10/2011 | Lang et al. | |
| 8,062,302 B2 | 11/2011 | Lang et al. | |
| 8,066,708 B2 | 11/2011 | Lang et al. | |
| 8,068,580 B2 | 11/2011 | Lang et al. | |
| 8,073,521 B2 | 12/2011 | Liew et al. | |
| 8,077,950 B2 | 12/2011 | Tsougarakis et al. | |
| 8,083,745 B2 | 12/2011 | Lang et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,234,097 B2 | 7/2012 | Steines et al. | |
| 8,260,018 B2 | 9/2012 | Lang et al. | |
| 8,290,564 B2 | 10/2012 | Lang et al. | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis, Jr. et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski et al. | |
| 8,545,569 B2 | 10/2013 | Fitz et al. | |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,585,708 B2 | 11/2013 | Fitz et al. | |
| 8,588,365 B2 | 11/2013 | Lang et al. | |
| 8,600,124 B2 | 12/2013 | Arnaud et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,625,874 B2 | 1/2014 | Lang et al. | |
| 8,634,617 B2 | 1/2014 | Tsougarakis et al. | |
| 8,638,998 B2 | 1/2014 | Steines et al. | |
| 8,639,009 B2 | 1/2014 | Lang et al. | |
| 8,641,716 B2 | 2/2014 | Fitz et al. | |
| 8,649,481 B2 | 2/2014 | Lang et al. | |
| 8,657,827 B2 | 2/2014 | Fitz et al. | |
| 8,682,052 B2 | 3/2014 | Fitz et al. | |
| 8,690,945 B2 | 4/2014 | Fitz et al. | |
| 8,690,955 B2 * | 4/2014 | Rolston | A61F 2/389 623/20.32 |
| 8,709,089 B2 | 4/2014 | Lang et al. | |
| 8,735,773 B2 | 5/2014 | Lang | |
| 8,768,028 B2 | 7/2014 | Lang et al. | |
| 8,771,365 B2 | 7/2014 | Bojarski et al. | |
| 8,781,191 B2 | 7/2014 | Lang et al. | |
| 8,818,484 B2 | 8/2014 | Liew et al. | |
| 8,882,847 B2 | 11/2014 | Burdulis, Jr. et al. | |
| 8,906,107 B2 | 12/2014 | Bojarski et al. | |
| 8,913,818 B2 | 12/2014 | Lang et al. | |
| 8,926,706 B2 | 1/2015 | Bojarski et al. | |
| 8,932,363 B2 | 1/2015 | Tsougarakis et al. | |
| 8,939,917 B2 | 1/2015 | Vargas-Voracek | |
| 8,945,230 B2 | 2/2015 | Lang et al. | |
| 8,951,259 B2 | 2/2015 | Fitz et al. | |
| 8,951,260 B2 | 2/2015 | Lang et al. | |
| 8,965,075 B2 | 2/2015 | Arnaud et al. | |
| 8,965,087 B2 | 2/2015 | Arnaud et al. | |
| 8,965,088 B2 | 2/2015 | Tsougarakis et al. | |
| 8,974,539 B2 | 3/2015 | Bojarski et al. | |
| 8,998,915 B2 | 4/2015 | Fitz et al. | |
| 9,020,788 B2 | 4/2015 | Lang et al. | |
| 9,023,050 B2 | 5/2015 | Lang et al. | |
| 9,055,953 B2 | 6/2015 | Lang et al. | |
| 9,066,728 B2 | 6/2015 | Burdulis, Jr. et al. | |
| 9,072,531 B2 | 7/2015 | Fitz et al. | |
| 9,084,617 B2 | 7/2015 | Lang et al. | |
| 9,095,353 B2 | 8/2015 | Burdulis, Jr. et al. | |
| 9,107,679 B2 | 8/2015 | Lang et al. | |
| 9,107,680 B2 | 8/2015 | Fitz et al. | |
| 9,113,921 B2 | 8/2015 | Lang et al. | |
| 9,125,672 B2 | 9/2015 | Fitz et al. | |
| 9,125,673 B2 | 9/2015 | Fitz et al. | |
| 9,155,501 B2 | 10/2015 | Lang et al. | |
| 9,180,015 B2 | 11/2015 | Fitz et al. | |
| 9,186,161 B2 | 11/2015 | Lang et al. | |
| 9,186,254 B2 | 11/2015 | Fitz et al. | |
| 9,216,025 B2 | 12/2015 | Fitz et al. | |
| 9,220,516 B2 | 12/2015 | Lang et al. | |
| 9,220,517 B2 | 12/2015 | Lang et al. | |
| 9,241,724 B2 | 1/2016 | Lang et al. | |
| 9,241,725 B2 | 1/2016 | Lang et al. | |
| 9,267,955 B2 | 2/2016 | Lang et al. | |
| 9,275,469 B2 | 3/2016 | Lang et al. | |
| 9,295,481 B2 | 3/2016 | Fitz et al. | |
| 9,295,482 B2 | 3/2016 | Fitz et al. | |
| 9,308,005 B2 | 4/2016 | Fitz et al. | |
| 9,308,053 B2 | 4/2016 | Bojarski et al. | |
| 9,308,091 B2 | 4/2016 | Lang | |
| 9,314,256 B2 | 4/2016 | Fitz et al. | |
| 9,408,705 B2 * | 8/2016 | Oosthuizen | A61F 2/389 |
| 9,526,633 B2 * | 12/2016 | Goodfellow | A61F 2/3868 |
| 2002/0186818 A1 | 12/2002 | Arnaud et al. | |
| 2003/0055502 A1 | 3/2003 | Lang et al. | |
| 2004/0006393 A1 * | 1/2004 | Burkinshaw | A61F 2/38 623/20.3 |

(56) References Cited

U.S. PATENT DOCUMENTS

| | | | |
|---|---|---|---|
| 2004/0006394 A1* | 1/2004 | Lipman | A61F 2/3868 623/20.29 |
| 2004/0106868 A1 | 6/2004 | Liew et al. | |
| 2004/0133276 A1 | 7/2004 | Lang et al. | |
| 2004/0193280 A1* | 9/2004 | Webster | A61F 2/3868 623/20.33 |
| 2005/0055100 A1* | 3/2005 | Lewis | A61F 2/38 623/20.28 |
| 2005/0209703 A1* | 9/2005 | Fell | A61F 2/38 623/20.33 |
| 2006/0111722 A1 | 5/2006 | Bouadi | |
| 2007/0047794 A1 | 3/2007 | Lang | |
| 2007/0083266 A1 | 4/2007 | Lang et al. | |
| 2007/0100462 A1 | 5/2007 | Lang et al. | |
| 2007/0156171 A1 | 7/2007 | Lang et al. | |
| 2007/0233269 A1 | 10/2007 | Steines et al. | |
| 2008/0058613 A1 | 3/2008 | Lang et al. | |
| 2008/0077003 A1 | 3/2008 | Barth et al. | |
| 2008/0091272 A1* | 4/2008 | Aram | A61F 2/3868 623/20.34 |
| 2008/0097794 A1 | 4/2008 | Arnaud et al. | |
| 2008/0183291 A1* | 7/2008 | Scheller | A61F 2/3872 623/14.12 |
| 2008/0195216 A1 | 8/2008 | Philipp | |
| 2008/0219412 A1 | 9/2008 | Lang | |
| 2009/0084491 A1* | 4/2009 | Uthgenannt | A61F 2/389 156/153 |
| 2009/0222103 A1 | 9/2009 | Fitz et al. | |
| 2009/0225958 A1 | 9/2009 | Lang | |
| 2009/0228113 A1 | 9/2009 | Lang et al. | |
| 2010/0217270 A1 | 8/2010 | Polinski et al. | |
| 2010/0274534 A1* | 10/2010 | Steines | A61B 17/1675 703/1 |
| 2010/0329530 A1 | 12/2010 | Lang et al. | |
| 2011/0071645 A1 | 3/2011 | Bojarski et al. | |
| 2011/0071802 A1 | 3/2011 | Bojarski et al. | |
| 2011/0082548 A1* | 4/2011 | Assell | A61F 2/30756 623/14.12 |
| 2011/0087332 A1 | 4/2011 | Bojarski et al. | |
| 2011/0144760 A1 | 6/2011 | Wong et al. | |
| 2011/0153286 A1 | 6/2011 | Zaeuner et al. | |
| 2011/0190898 A1* | 8/2011 | Lenz | A61F 2/38 623/20.32 |
| 2011/0213368 A1 | 9/2011 | Fitz et al. | |
| 2011/0213374 A1 | 9/2011 | Fitz et al. | |
| 2011/0213377 A1 | 9/2011 | Lang et al. | |
| 2011/0213427 A1 | 9/2011 | Fitz et al. | |
| 2011/0213428 A1 | 9/2011 | Fitz et al. | |
| 2011/0213429 A1 | 9/2011 | Lang et al. | |
| 2011/0218539 A1 | 9/2011 | Fitz et al. | |
| 2011/0218635 A1* | 9/2011 | Amis | A61F 2/38 623/20.18 |
| 2011/0238073 A1 | 9/2011 | Lang et al. | |
| 2011/0313423 A1 | 12/2011 | Lang et al. | |
| 2012/0066892 A1 | 3/2012 | Lang et al. | |
| 2012/0071883 A1 | 3/2012 | Lang et al. | |
| 2012/0072185 A1 | 3/2012 | Lang et al. | |
| 2012/0151730 A1 | 6/2012 | Fitz et al. | |
| 2012/0191205 A1 | 7/2012 | Bojarski et al. | |
| 2012/0191206 A1* | 7/2012 | Stein | A61B 5/01 623/20.32 |
| 2012/0191420 A1 | 7/2012 | Bojarski et al. | |
| 2012/0197260 A1 | 8/2012 | Fitz et al. | |
| 2012/0197408 A1 | 8/2012 | Lang et al. | |
| 2012/0209394 A1 | 8/2012 | Bojarski et al. | |
| 2012/0226359 A1* | 9/2012 | Stein | A61F 2/4657 623/20.32 |
| 2012/0245699 A1 | 9/2012 | Lang et al. | |
| 2012/0323334 A1 | 12/2012 | Jones et al. | |
| 2012/0323337 A1 | 12/2012 | Parisi et al. | |
| 2012/0330431 A1* | 12/2012 | Rolston | A61F 2/389 623/20.32 |
| 2013/0103363 A1 | 4/2013 | Lang et al. | |
| 2013/0110471 A1 | 5/2013 | Lang et al. | |
| 2013/0184713 A1 | 7/2013 | Bojarski et al. | |
| 2013/0195325 A1 | 8/2013 | Lang et al. | |
| 2013/0197870 A1 | 8/2013 | Steines et al. | |
| 2013/0204384 A1 | 8/2013 | Hensley et al. | |
| 2013/0211410 A1 | 8/2013 | Landes et al. | |
| 2013/0211531 A1 | 8/2013 | Steines et al. | |
| 2013/0245803 A1 | 9/2013 | Lang | |
| 2013/0253522 A1 | 9/2013 | Bojarsk et al. | |
| 2013/0289570 A1 | 10/2013 | Chao | |
| 2013/0296874 A1 | 11/2013 | Chao | |
| 2013/0297031 A1 | 11/2013 | Hafez | |
| 2013/0317619 A1* | 11/2013 | Goodfellow | A61F 2/3868 623/20.3 |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031826 A1 | 1/2014 | Bojarski et al. | |
| 2014/0058396 A1 | 2/2014 | Fitz et al. | |
| 2014/0066935 A1 | 3/2014 | Fitz et al. | |
| 2014/0067076 A1* | 3/2014 | Collazo | A61F 2/389 623/20.32 |
| 2014/0086780 A1 | 3/2014 | Miller et al. | |
| 2014/0109384 A1 | 4/2014 | Lang | |
| 2014/0115872 A1 | 5/2014 | Steines et al. | |
| 2014/0126800 A1 | 5/2014 | Lang et al. | |
| 2014/0136154 A1 | 5/2014 | Bojarski et al. | |
| 2014/0142710 A1 | 5/2014 | Lang | |
| 2014/0153810 A1 | 6/2014 | Lang et al. | |
| 2014/0163568 A1 | 6/2014 | Wong et al. | |
| 2014/0172111 A1 | 6/2014 | Lang et al. | |
| 2014/0188240 A1 | 7/2014 | Lang et al. | |
| 2014/0194996 A1 | 7/2014 | Bojarski et al. | |
| 2014/0208578 A1 | 7/2014 | Linderman et al. | |
| 2014/0222157 A1 | 8/2014 | Al Hares et al. | |
| 2014/0222390 A1 | 8/2014 | Asseln et al. | |
| 2014/0228860 A1 | 8/2014 | Steines et al. | |
| 2014/0236308 A1* | 8/2014 | Oosthuizen | A61F 2/389 623/20.28 |
| 2014/0250676 A1 | 9/2014 | Lang et al. | |
| 2014/0250677 A1 | 9/2014 | Lang | |
| 2014/0257508 A1 | 9/2014 | Bojarski et al. | |
| 2014/0259629 A1 | 9/2014 | Dion et al. | |
| 2014/0263674 A1 | 9/2014 | Cerveny | |
| 2014/0277548 A1* | 9/2014 | Cohen | A61F 2/389 623/20.34 |
| 2014/0303629 A1 | 10/2014 | Lang et al. | |
| 2014/0330389 A1* | 11/2014 | Jordan | A61F 2/30767 623/20.34 |
| 2014/0336774 A1 | 11/2014 | Fitz et al. | |
| 2014/0343681 A1* | 11/2014 | Cohen | A61F 2/389 623/20.32 |
| 2014/0355852 A1 | 12/2014 | Liew et al. | |
| 2014/0364857 A1 | 12/2014 | Bojarski et al. | |
| 2014/0371866 A1 | 12/2014 | Chao et al. | |
| 2015/0032215 A1 | 1/2015 | Slamin et al. | |
| 2015/0032217 A1 | 1/2015 | Bojarski et al. | |
| 2015/0057756 A1 | 2/2015 | Lang et al. | |
| 2015/0081029 A1 | 3/2015 | Bojarski et al. | |
| 2015/0093283 A1 | 4/2015 | Miller et al. | |
| 2015/0150644 A1 | 6/2015 | Lang et al. | |
| 2015/0157461 A1 | 6/2015 | Burdulis, Jr. et al. | |
| 2015/0178918 A1 | 6/2015 | Arnaud et al. | |
| 2015/0182342 A1 | 7/2015 | Hafez | |
| 2015/0190234 A1* | 7/2015 | Wei | A61F 2/389 623/20.32 |
| 2015/0213645 A1 | 7/2015 | Siebarth et al. | |
| 2015/0216615 A1 | 8/2015 | Tsougarakis et al. | |
| 2015/0223941 A1 | 8/2015 | Lang | |
| 2015/0250552 A1 | 9/2015 | Radermacher et al. | |
| 2015/0250597 A1 | 9/2015 | Lang et al. | |
| 2015/0342741 A1* | 12/2015 | Davignon | A61F 2/389 623/20.32 |
| 2016/0008136 A1* | 1/2016 | Jones | A61F 2/389 623/20.17 |

(56) References Cited

U.S. PATENT DOCUMENTS

2016/0015465 A1   1/2016   Steines et al.
2016/0038293 A1   2/2016   Slamin et al.
2016/0045317 A1   2/2016   Lang et al.

FOREIGN PATENT DOCUMENTS

| Country | Number | Date |
|---|---|---|
| AU | 2014200073 | 1/2014 |
| AU | 2015202416 | 5/2015 |
| AU | 2015203126 | 6/2015 |
| AU | 2015203709 | 7/2015 |
| AU | 2015203808 | 7/2015 |
| AU | 2015203823 | 7/2015 |
| CA | 2804883 | 6/2005 |
| CA | 2546965 | 3/2013 |
| CN | 102599960 | 7/2012 |
| CN | 102805677 | 11/2015 |
| DE | 10064111 A1 | 7/2002 |
| DE | 102007034221 A1 | 4/2008 |
| DE | 102013208892 A1 | 5/2014 |
| EP | 1951136 A1 | 8/2008 |
| EP | 2124764 A1 | 12/2009 |
| EP | 2265199 A1 | 12/2010 |
| EP | 2303193 A1 | 4/2011 |
| EP | 2403434 A1 | 1/2012 |
| EP | 2405865 A2 | 1/2012 |
| EP | 2419035 A1 | 2/2012 |
| EP | 2512381 A2 | 10/2012 |
| EP | 2591756 A1 | 5/2013 |
| EP | 2754419 A2 | 7/2014 |
| WO | 0217789 | 3/2002 |
| WO | 0230283 | 4/2002 |
| WO | 02096268 | 12/2002 |
| WO | 02096284 | 12/2002 |
| WO | 2004019256 | 3/2004 |
| WO | 2004049981 | 6/2004 |
| WO | 2004062495 | 7/2004 |
| WO | 2004086972 | 10/2004 |
| WO | 2005027732 | 3/2005 |
| WO | 2005051239 | 6/2005 |
| WO | 2006034018 | 3/2006 |
| WO | 2006058057 | 6/2006 |
| WO | 2006060795 | 6/2006 |
| WO | 2007041375 | 4/2007 |
| WO | 2007062079 | 5/2007 |
| WO | 2007109641 | 9/2007 |
| WO | 2010151564 | 12/2010 |
| WO | 2011028624 | 3/2011 |
| WO | 2011056995 | 5/2011 |
| WO | WO2011075697 A2 | 6/2011 |
| WO | 2011134440 | 11/2011 |
| WO | WO2012027150 A2 | 3/2012 |
| WO | WO2012027185 A1 | 3/2012 |
| WO | 2013025814 | 2/2013 |
| WO | 2013152341 | 10/2013 |
| WO | 2013155500 | 10/2013 |
| WO | 2014008444 | 1/2014 |
| WO | 2014145267 | 9/2014 |
| WO | 2014145281 | 9/2014 |
| WO | 2014150428 | 9/2014 |
| WO | 2014152533 | 9/2014 |
| WO | 2014153530 | 9/2014 |
| WO | 2015112566 | 7/2015 |
| WO | 2015112570 | 7/2015 |
| WO | 2015162543 | 10/2015 |

\* cited by examiner

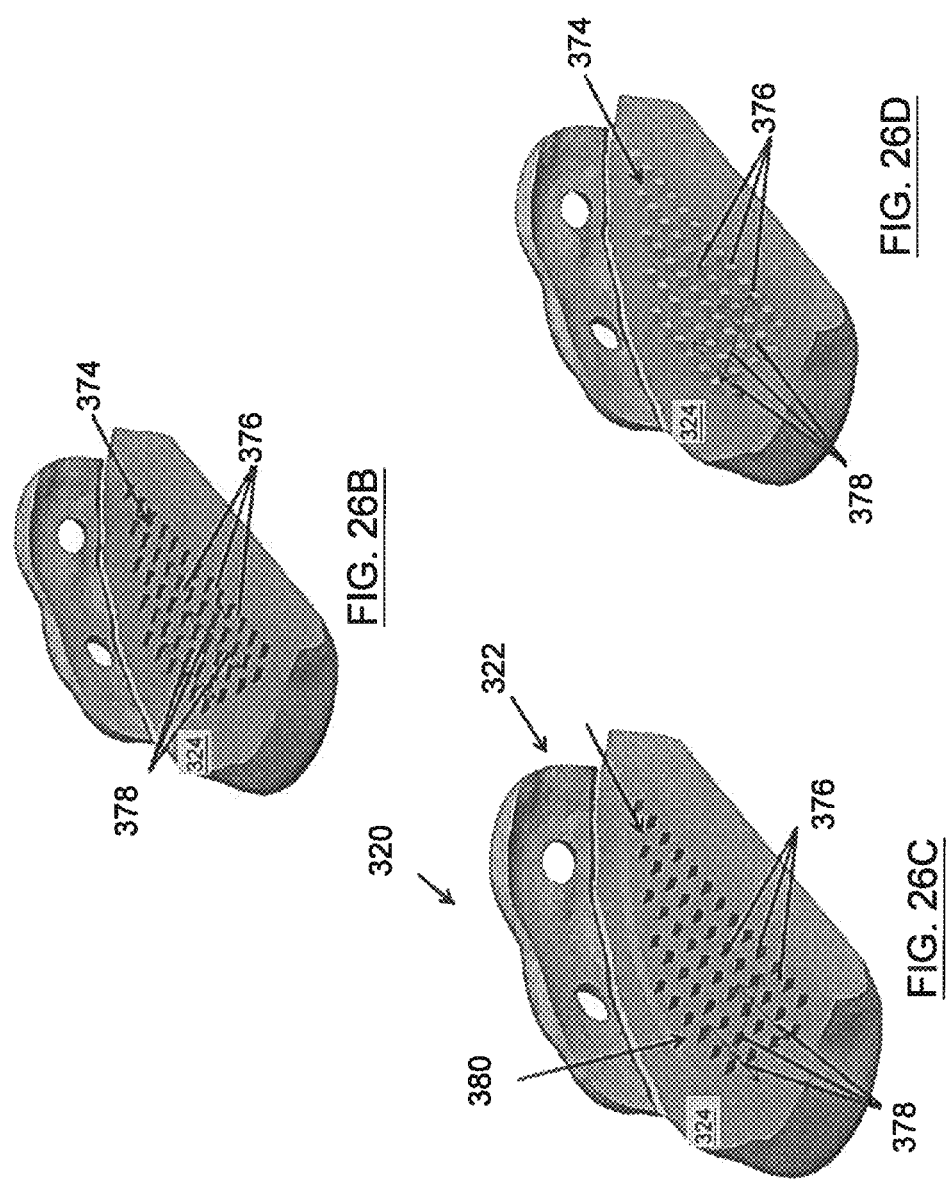

ANATOMICALLY ADAPTED ORTHOPEDIC IMPLANT AND METHOD OF MANUFACTURING SAME

CROSS-REFERENCE TO RELATED APPLICATIONS

This application claims the priority benefit of U.S. provisional application 62/017,933 filed on Jun. 27, 2014. This application is a continuation-in-part application of international application PCT/CA2014/050797 filed on Aug. 20, 2014, which claims the priority benefit of U.S. provisional application 61/868,236 filed on Aug. 21, 2013. U.S. provisional application 61/868,236, U.S. provisional application 62/017,933, and international application PCT/CA2014/050797 are hereby expressly incorporated by reference in their entirety.

FIELD OF THE INVENTION

The present invention relates to the field of orthopedic implants. More particularly, it relates to an anatomically adapted orthopedic implant with at least one retention section and a bone facing surface shaped to match a surface of a corresponding bone of a patient. The invention also relates to a method of manufacturing the same.

BACKGROUND

Prostheses are commonly used to repair and/or replace damaged bones and tissues in the human body. It is typical to repair diseased, injured or defective joints with standard off-the-shelf orthopedic implants (or prosthesis). However, standard off-the-shelf orthopedic implants usually do not fit on patient's existing or healthy biological structure. Therefore, patient's biological structure usually must be resected to fit the standard off-the-shelf orthopedic implant. For several reasons, resecting existing or healthy biological structure is not optimal and there is thus a need for patient's adapted orthopedic implants.

Furthermore, when implanting orthopedic implants, such as a femoral or a tibial orthopedic implant, it is typical to cut ligaments, such as anterior cruciate ligaments. Ligament cuts should however be minimized and, when possible, avoided.

In view of the above, there is a need for an improved anatomically adapted orthopedic implant and method of manufacture thereof which would be able to overcome or at least minimize some of the above-discussed prior art concerns.

SUMMARY OF THE INVENTION

According to a general aspect, there is provided an orthopedic implant to cover at least partially a surface of a bone of a patient. The orthopedic implant comprises a body having at least one retaining section, a bone-facing surface, and an articular surface. The at least one retaining section is configured to retain the orthopedic implant on the surface of the patient's bone along at least one axis by covering a corresponding retaining surface thereof and the bone-facing surface of at least one of the at least one retaining section nestingly conforms to an unresected portion of the surface of the bone of the patient.

In an embodiment, the bone-facing surface of the at least one retaining section is free of planar section.

In an embodiment, the at least one retaining section extends inwardly towards a center of the bone and at least one of upwardly and downwardly from a section covering an articular section of the surface of the bone.

In an embodiment, the bone-facing surface of the body is configured to nestingly conform to the surface of the bone of the patient. The bone-facing surface of the body can be configured to nestingly conform to a cartilage-free portion of the surface of the bone of the patient.

In an embodiment, the body is substantially C-shaped along at least one axis.

In an embodiment, the articular surface is conform to a cartilage portion of the surface of the bone of the patient.

In an embodiment, the articular surface is an offset of one of a cartilage portion of the surface of the bone of the patient and the surface of the bone of the patient.

In an embodiment, the articular surface is conform to a corrected cartilage portion of the surface of the bone of the patient.

In an embodiment, the orthopedic implant is a femoral implant.

In an embodiment, the orthopedic implant is a tibial implant.

According to another general aspect, there is provided a femoral orthopedic implant for implantation into a patient's femoral knee joint. The femoral orthopedic implant comprises a body being configured to be self-retaining along at least one axis and having a bone-facing surface, an articular surface and a retaining section. The bone-facing surface of the body nestingly conforms to a corresponding unresected and cartilage-free portion of a surface of a distal femur of the patient and the retaining section covers an unresected retaining surface of the distal femur of the patient.

In an embodiment, the bone-facing surface is a concave surface.

In an embodiment, the body is substantially C-shaped along at least one axis. Free ends of the body can define a restricted passage along a sagittal plane of the patient.

In an embodiment, the articular surface reproduces a cartilage portion of the femoral knee joint of the patient.

In an embodiment, the articular surface is an offset reproduction of one of a cartilage portion of the femoral knee joint of the patient and the surface of the distal femur of the patient.

In an embodiment, the articular surface is a corrected reproduction of a cartilage portion of the femoral knee joint of the patient.

In an embodiment, the bone-facing surface is free of planar section.

In an embodiment, the retaining section extends inwardly towards a center of the distal femur and upwardly from a section covering an articular section of the surface of the distal femur.

According to still another general aspect, there is provided a femoral orthopedic implant for implantation into a patient's femoral knee joint. The femoral orthopedic implant comprises a body having a bone-facing surface nestingly conforming to an entire corresponding unresected and cartilage-free portion of a surface of a distal femur of the patient.

In an embodiment, the bone facing surface is free of planar section.

In an embodiment, the body further comprises a retaining section covering a retaining surface of the distal femur of the patient to retain the femoral orthopedic implant onto the distal femur along at least one axis when implanted thereon. The retaining section can extend inwardly towards a center of the distal femur and upwardly from a section covering an articular section of the surface of the distal femur.

In an embodiment, the bone-facing surface is a concave surface.

In an embodiment, the body is substantially C-shaped along at least one axis. Free ends of the body can define a restricted passage along a sagittal plane of the patient.

According to a further general aspect, there is provided a tibial orthopedic implant for implantation into a patient's tibial knee joint. The tibial orthopedic implant comprises a body having a bone-facing surface, an articular surface and at least one retaining section, each one of the at least one retaining section covering a corresponding retaining surface of a proximal tibia of the patient and retaining the body along at least one axis and the bone-facing surface of at least one of the at least one retaining section nestingly conforming to an unresected portion of the surface of the proximal tibia of the patient.

In an embodiment, the bone-facing surface of the body nestingly conforms to a corresponding cartilage-free portion of a surface of a proximal tibia of the patient.

In an embodiment, the at least one of the at least one retaining section nestingly conforming to an unresected portion of the surface of the proximal tibia of the patient comprises a substantially U-shaped flange extending downwardly and inwardly towards the proximal tibia.

In an embodiment, the body comprises at least two retaining sections and wherein the bone-facing surface of at least one of the at least two retaining sections nestingly The at least two retaining sections can retain the body along at least two axes, perpendicular to one another.

In an embodiment, the articular surface reproduces a cartilage portion of the tibial knee joint of the patient.

In an embodiment, the articular surface is an offset reproduction of one of a cartilage portion of the tibial knee joint of the patient and the surface of the proximal tibia of the patient.

In an embodiment, the articular surface is a corrected reproduction of a cartilage portion of the tibial knee joint of the patient.

According to still another general aspect, there is provided a method for conceiving and implanting an orthopedic implant. The method comprises: obtaining an image of a structure of a patient's bone to be covered by the orthopedic implant; determining an unresected retaining surface on the structure of the patient's bone for the orthopedic implant; conceiving the orthopedic implant having a body with a bone-facing surface defining a retaining section nestingly conforming to the unresected retaining surface; and implanting the orthopedic implant on the structure of the patient's bone, the retaining section of the orthopedic implant covering the retaining surface of the structure of the patient's bone and retaining the orthopedic implant on the structure of the patient's bone along at least one axis.

In an embodiment, the unresected retaining surface is cartilage-free.

In an embodiment, the bone-facing surface of the retaining section is free of planar section.

In an embodiment, conceiving the orthopedic implant comprises conceiving the retaining section to extend inwardly towards a center of the bone and at least one of upwardly and downwardly from a section covering an articular section of the surface of the bone.

In an embodiment, conceiving the orthopedic implant comprises conceiving the bone-facing surface of the body to nestingly conform to the surface of the patient's bone.

In an embodiment, conceiving the orthopedic implant comprises conceiving the body to be substantially C-shaped along at least one axis.

According to another general aspect, there is also provided an implant for attachment to an implant region formed in remaining bone tissue following resection of a portion of a bone, the implant region having an application surface. The implant comprises: a body having a bone-facing surface abuttable against the application surface, an articulation plate engagement surface spaced apart from and opposite to the bone-facing surface, and an outer side surface extending between and connecting the bone-facing surface and the articulation plate engagement surface. The side surface has a side surface morphology matching an outer morphology of a corresponding surface of the resected portion of bone. The implant also comprises an attachment flange extending along at least a portion of the side surface and projecting away from the bone-facing surface along a longitudinal axis of the bone, the attachment flange defining an inner surface having an inner surface morphology matching an outer morphology of an outer surface of the bone for abutment thereagainst, the attachment flange having at least one hole extending transversely therethrough to receive an attachment device.

In an embodiment, the bone-facing surface includes at least one engagement member formed on the bone-facing surface along the longitudinal axis of the bone.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIG. 26B is a bottom perspective view of the base plate of the tibial orthopedic implant shown in FIG. 26, according to an embodiment where the bone-facing surface is free of fixation pegs and has a surface pattern;

FIG. 26C is a bottom perspective view of the base plate of the tibial orthopedic implant shown in FIG. 26B, according to an embodiment where the surface pattern of the bone-facing surface has a different configuration;

FIG. 26D is a bottom perspective view of the base plate of the tibial orthopedic implant shown in FIG. 26B, according to an embodiment where the surface pattern of the bone-facing surface again has a different configuration;

DETAILED DESCRIPTION

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of the anatomically adapted prosthesis, or orthopedic implant and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation therein between, as well as other suitable geometrical configurations, can be used for the anatomically adapted orthopedic implant, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

The present disclosure provides orthopedic implants (or prosthesis) which contribute to preservation of healthy bones, enhanced articular characteristics, and reduced impact on soft tissues such as ligaments.

In the disclosure, the term "proximal" refers to a direction generally located toward the center of the body and nearest the point of attachment to the body. By opposition, the term "distal" refers to a direction away from the center of the body. In other words, in reference with a patient, the term "proximal" refers to a direction generally towards the torso of the patient and "distal" refers to a direction opposite of proximal, i.e. away from the torso of the patient. The term "anterior" refers to a direction generally toward the front of a patient and "posterior" refers to the opposite direction of anterior, i.e. toward the back of the patient. In the context of an orthopedic implant alone, such directions correspond to the orientation of the orthopedic implant after implantation. Thus, for instance, the proximal portion of the orthopedic implant is the portion which will be closest to the torso of the patient.

Furthermore, the orthopedic implant can be referred to in the context of a coordinate system including transverse, coronal, and sagittal planes. Thus, upon implantation of the orthopedic implant a transverse plane of the orthopedic implant is generally parallel to the transverse plane of the patient, i.e. substantially horizontal. It is appreciated that, in some embodiments, upon implementation, the orthopedic implant planes can be slightly angled with respect to the corresponding anatomical planes.

Figure 1:
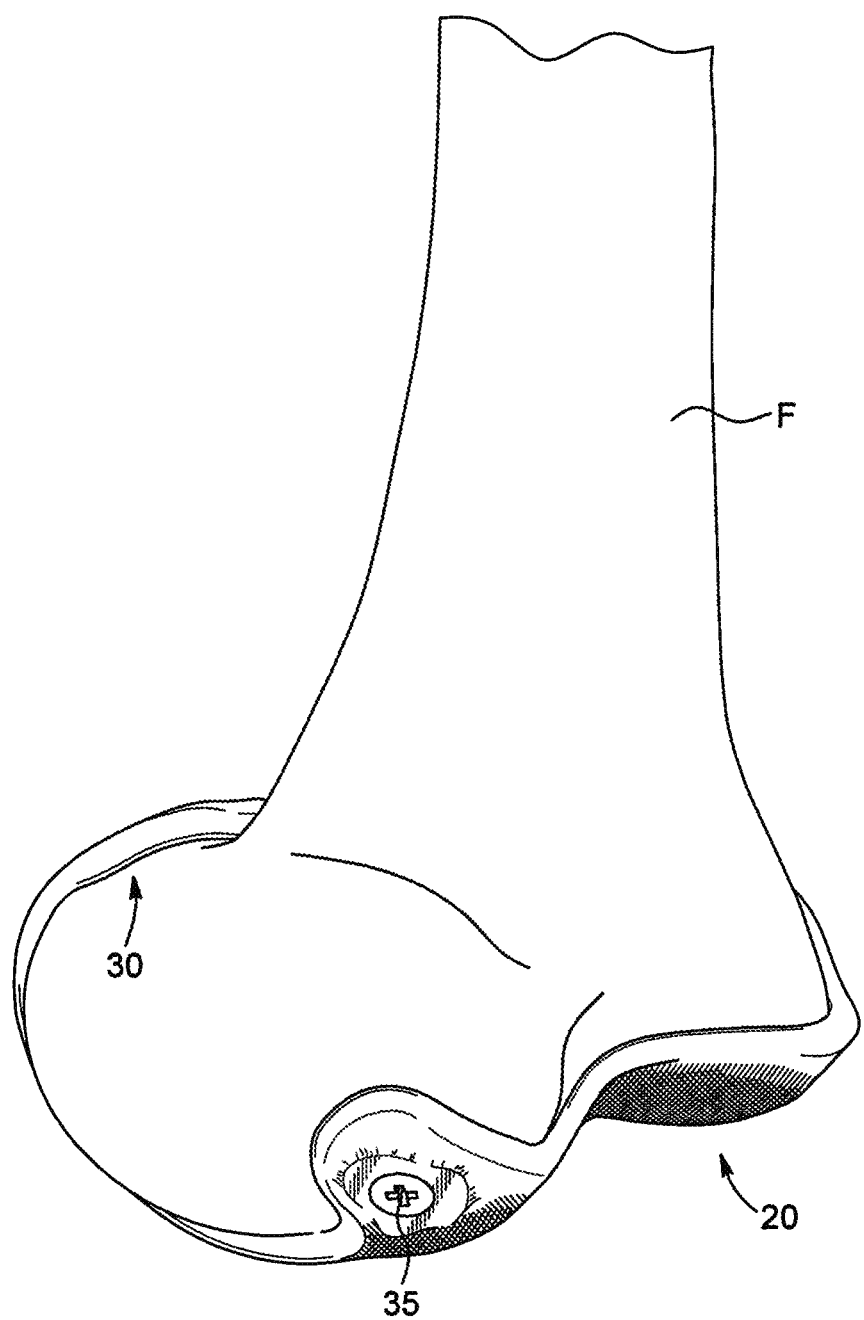
FIG. 1 is a rear perspective view of a bicompartmental femoral orthopedic implant implanted on a non-resected bone surface of a distal femur.
Figure 2:
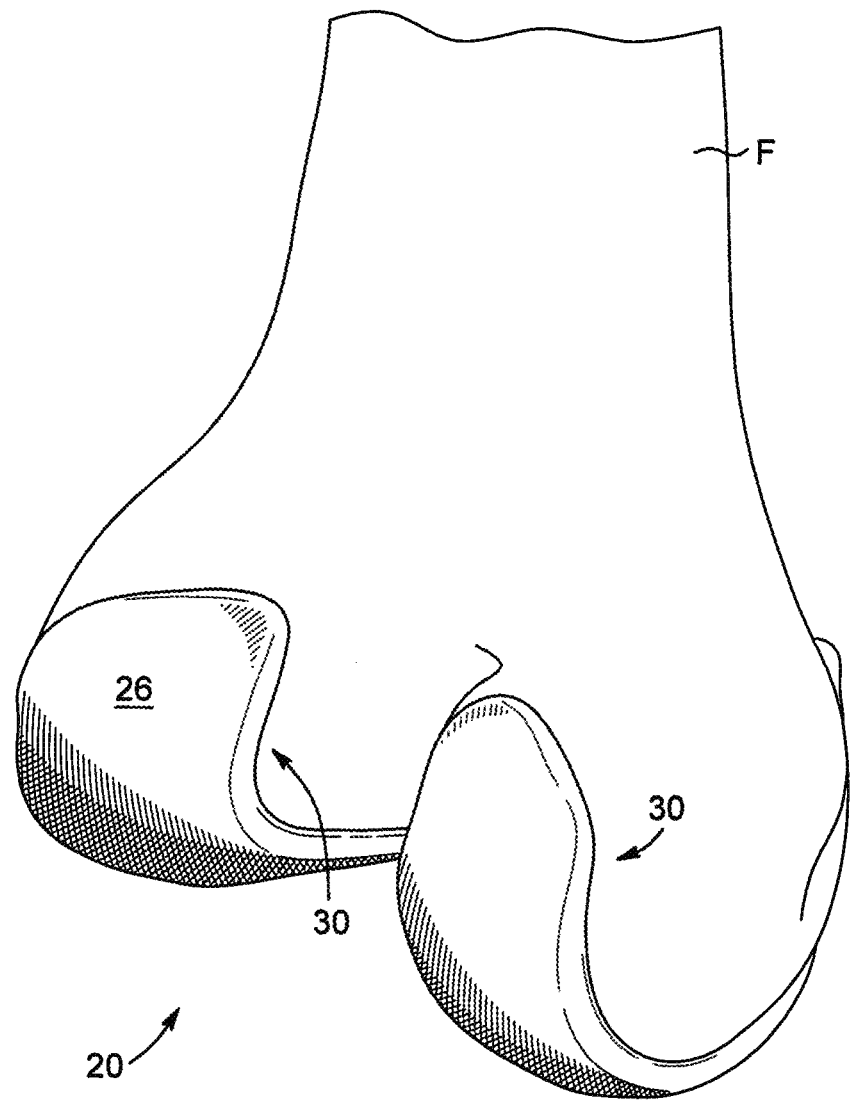
FIG. 2 is a front perspective view of the bicompartmental femoral orthopedic implant shown in FIG. 1, implanted on the non-resected bone surface of the distal femur.
Figure 3:
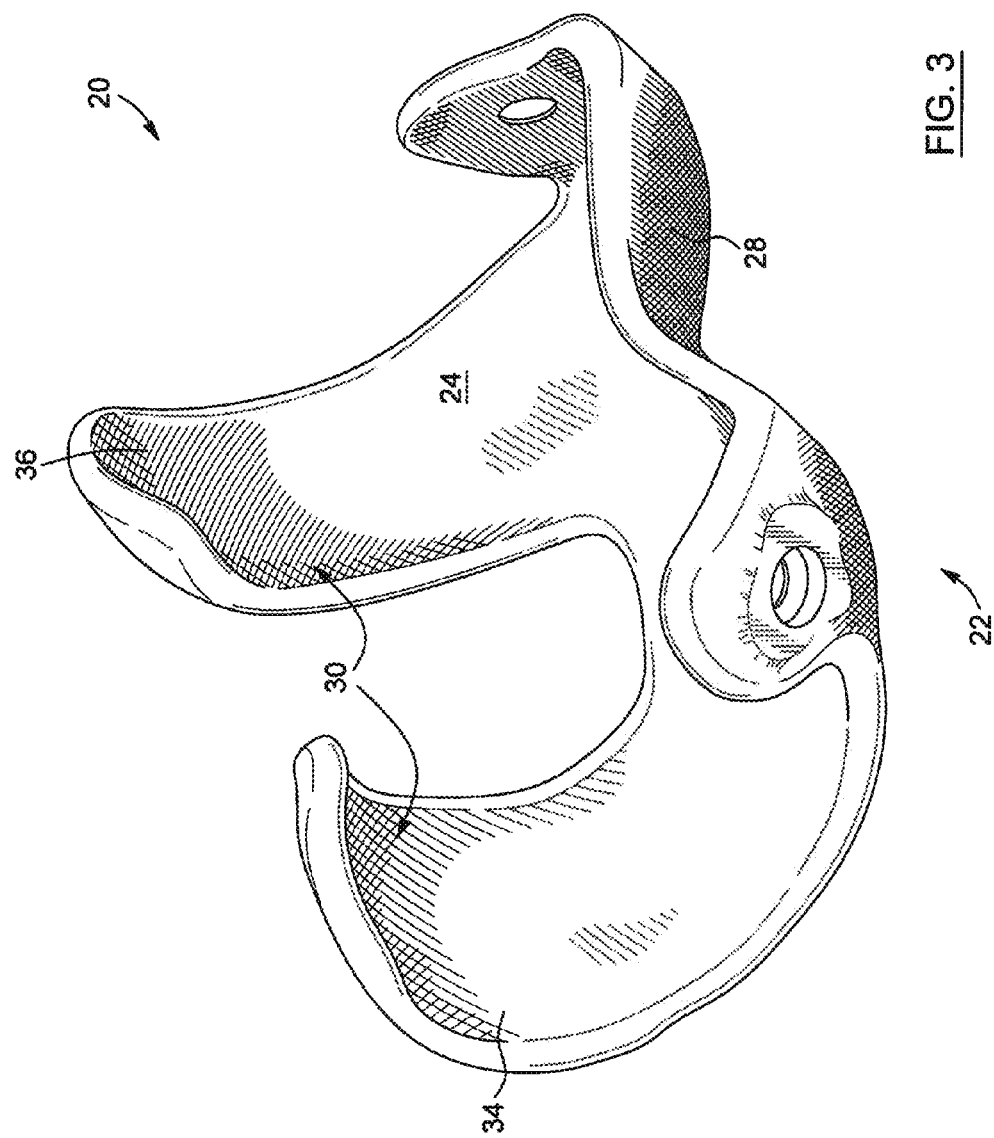
FIG. 3 is a top perspective view of the bicompartmental femoral orthopedic implant shown in FIG. 1, removed from the distal femur.
Figure 4:
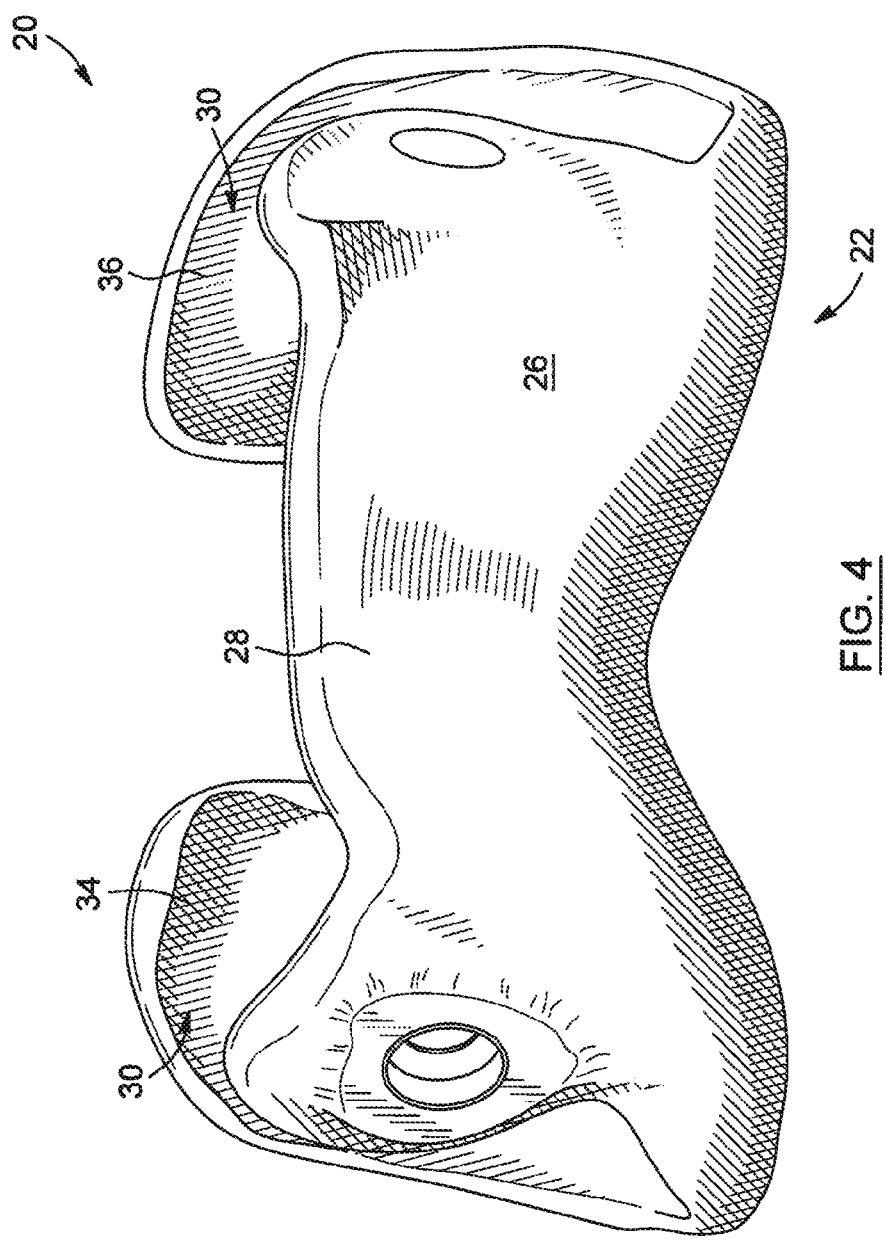
FIG. 4 is a rear elevation view of the bicompartmental femoral orthopedic implant shown in FIG. 3.
Figure 5:
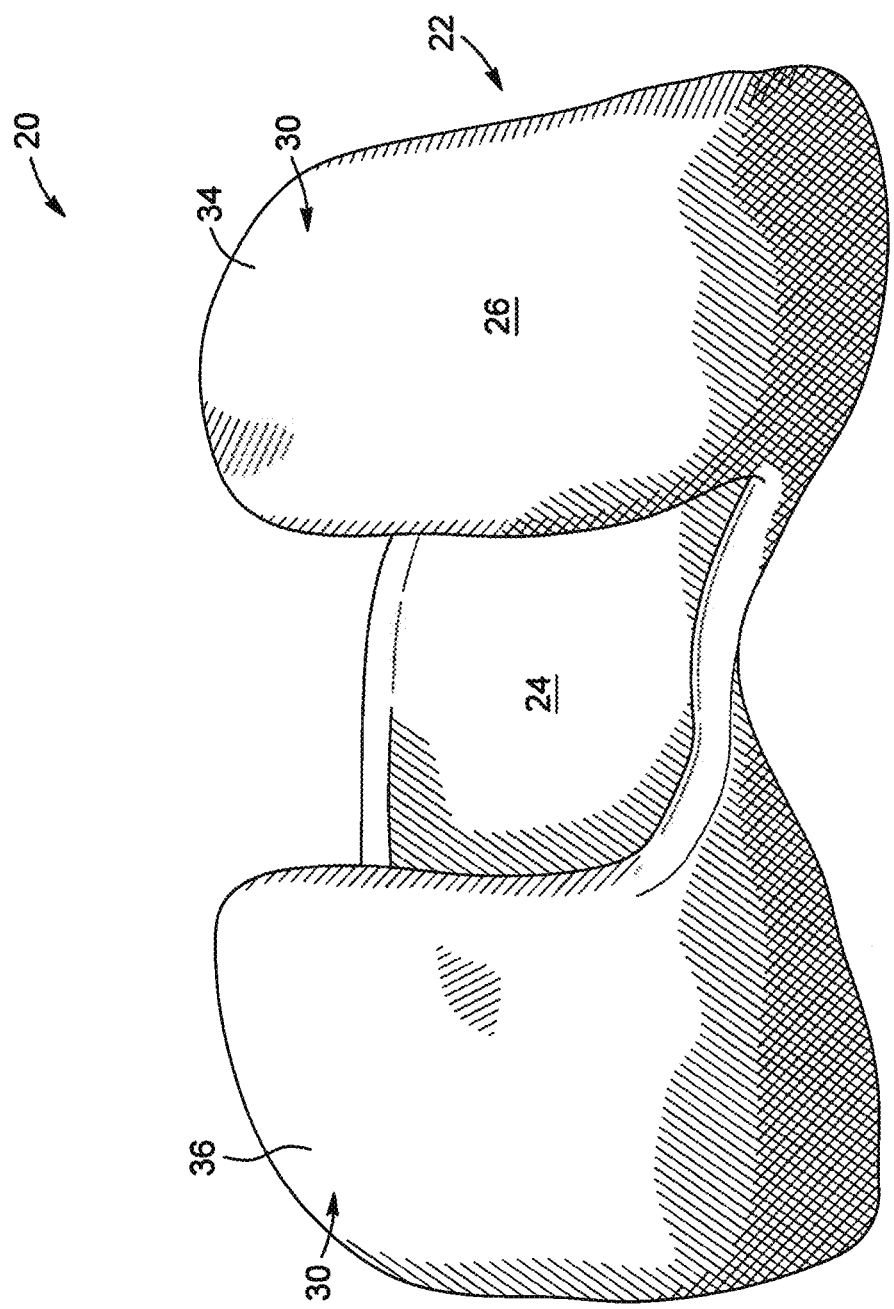
FIG. 5 is a front elevation view of the bicompartmental femoral orthopedic implant shown in FIG. 3.
Figure 6:
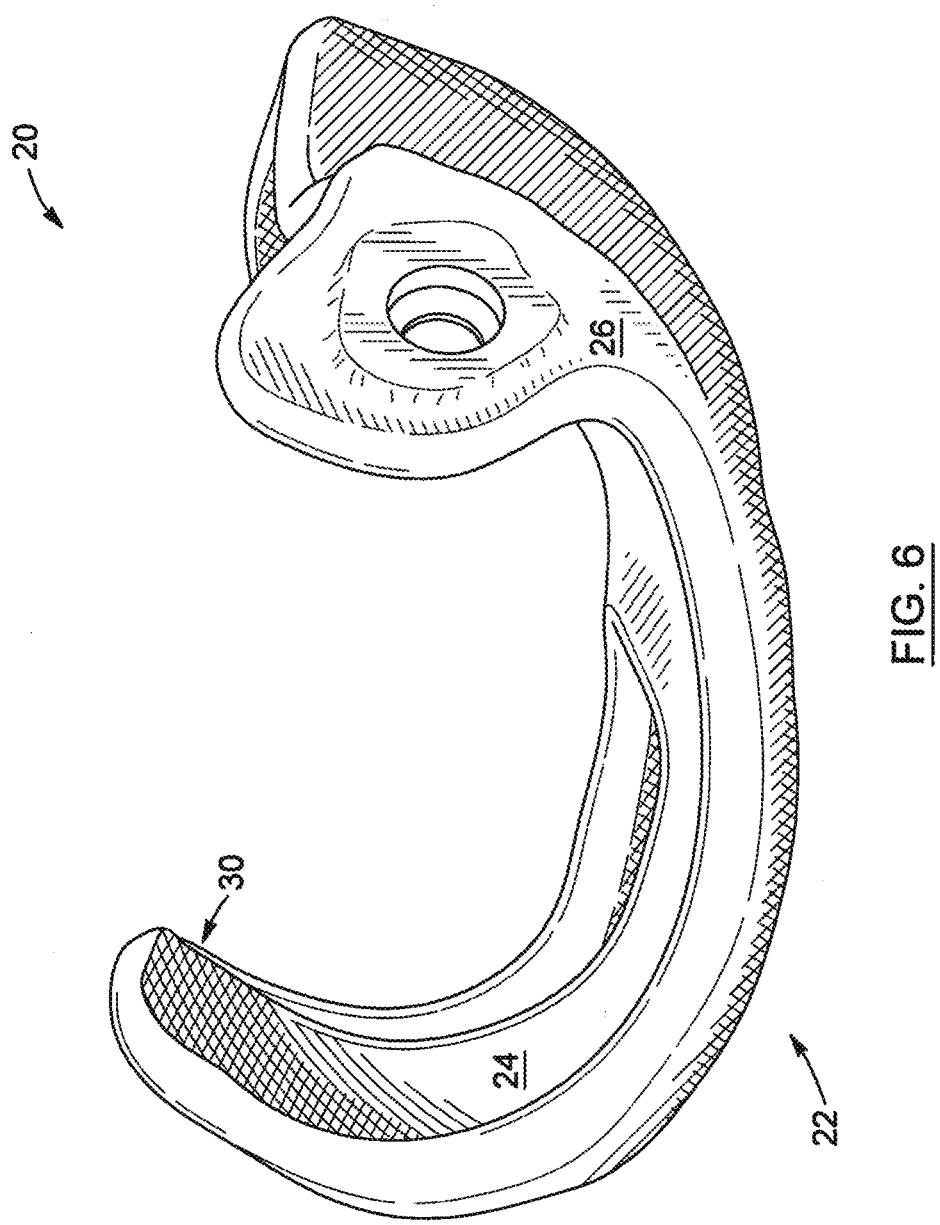
FIG. 6 is a side elevation view of the bicompartmental femoral orthopedic implant shown in FIG. 3.
Figure 7:
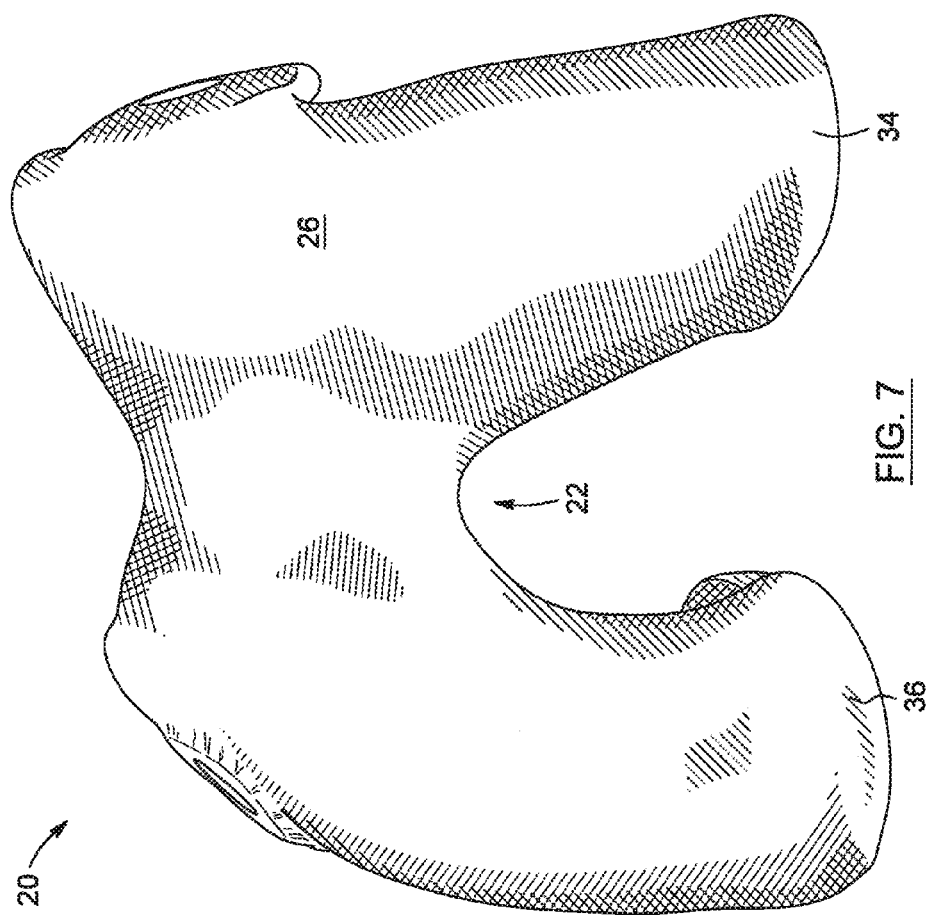
FIG. 7 is a bottom plan view of the bicompartmental femoral orthopedic implant shown in FIG. 3.
Figure 8:
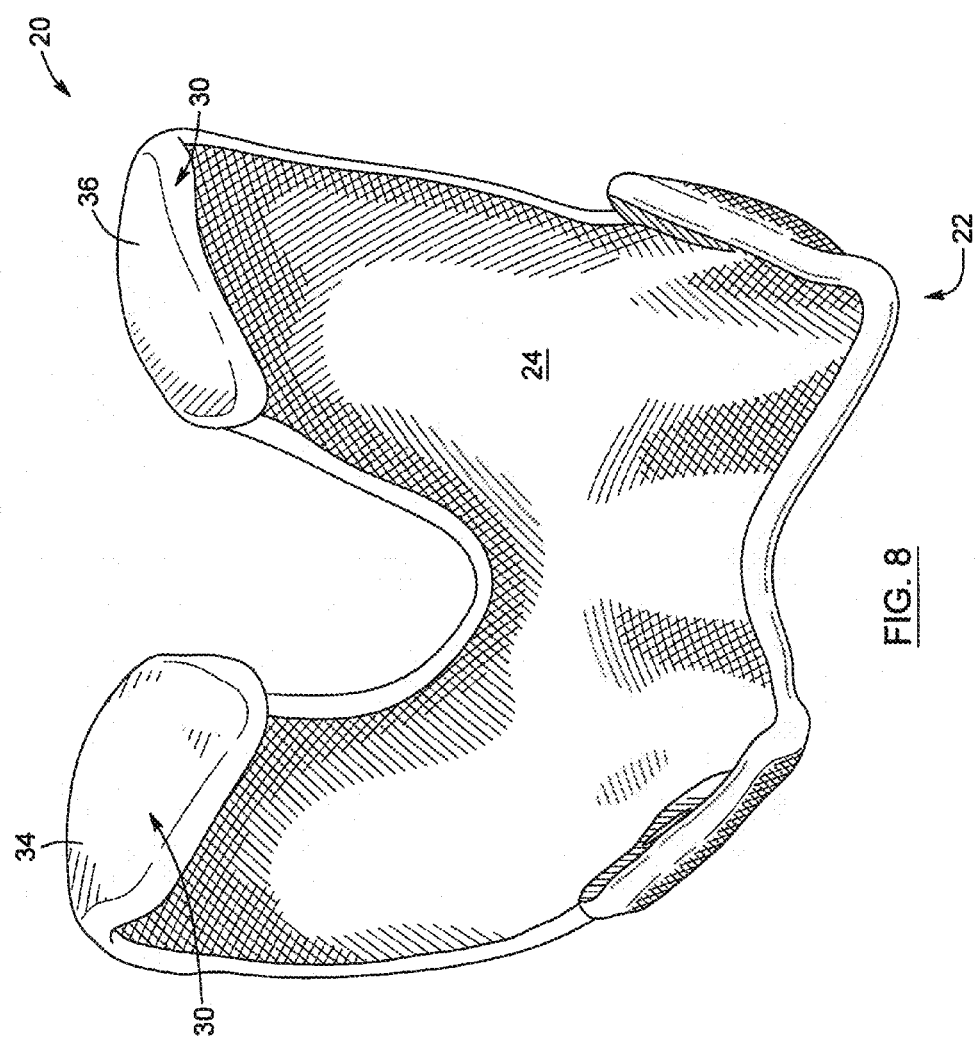
FIG. 8 is a top plan view of the bicompartmental femoral orthopedic implant shown in FIG. 3.

Referring now to the drawings and, more particularly, referring to FIGS. 1 and 2, in accordance with one embodiment, there is provided an anatomically adapted bicompartmental femoral orthopedic implant 20 for a femoral knee joint, i.e. an orthopedic implant designed to cover the lateral and medial femoral condyles by curving up around the distal end of the femur (or thighbone). More particularly, the bicompartmental femoral orthopedic implant 20 is mounted to a distal surface of a patient's femur F. As will be described in more details below, the distal surface of the patient's femur F is non-resected before implanting the femoral orthopedic implant 20 thereon, i.e. the femur bone is non-resected before implanting the orthopedic implant 20.

Referring now to FIGS. 3 to 8, there is shown that the bicompartmental femoral orthopedic implant 20 comprises a body 22 with a bone-facing surface 24 and an articulating surface 26, opposed to the bone-facing surface 24. In an embodiment, the body 22 of the implant 20 is made of a cobalt-chromium alloy. One skilled in the art will understand that, in alternative embodiments, the body 22 can also be made of other biocompatible materials.

The body 22 has an overall C-shaped profile. It includes an anterior flange 28 and two spaced-apart condyles 34, 36. In the embodiment shown, the bone-facing surface 24 is free of fixation pegs, as will be described in more details below.

In an embodiment, the bone-facing surface 24 is configured to be complementary to a portion of a patient's bone surface and nestingly conform thereto when engaged therewith. In other words, the bone-facing surface 24 is patient specific and can mate with the portion of the patient's bone surface in only one position. For instance, in the embodiment shown in FIGS. 1 to 8, the bone-facing surface 24 of the bicompartmental femoral orthopedic implant 20 matches entirely the surface of the distal end of the patient's femur F, without resection thereof. Therefore, it will be understood by a person skilled in the art that the shape of the bone-facing surface 24 will vary in accordance with the shape of the patient's bone.

In view of the above, it will be understood that in order to design the bicompartmental femoral orthopedic implant 20, including the bone-facing surface 24, an image of at least a portion of a body structure of the patient is previously obtained. The image of at least the portion of the body structure of the patient includes the bone on which the orthopedic implant 20 is to be implanted.

The image can be obtained using known imaging techniques, such as, without being limitative, magnetic resonance imaging (MRI), computed axial tomography (CAT scan), ultrasound, X-ray, or the like and various CAD software for the three-dimensional image reconstruction. Once the image of at least the portion of the patient body structure has been obtained, the patient-specific orthopedic implant 20 is designed and conceived. The orthopedic implant 20 is conceived with an orthopedic implant conception software. The bone-facing surface 24 is designed to fit the shape of the bone when the imaging of the patient body structure is carried out. The articulating surface 26 is also designed to be specific to the patient and can be designed to compensate for deficiencies, as will be described in more details below.

In the embodiment shown, the bone-facing surface 24 of the orthopedic implant 20 is planar surface free since it conforms to the shape of a non-resected bone.

Figure 10:
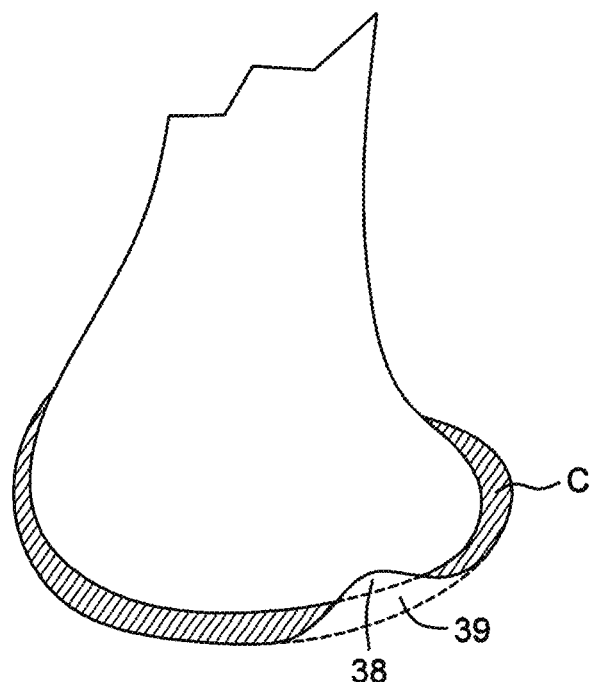
FIG. 10, is a cross sectional schematic representation of a distal femur with a missing cartilage portion and a missing bone portion.

The bone-facing surface 24 is designed to be juxtaposed to a section of the patient's bone. Thus, the bone-facing surface 24 is designed to be juxtaposed and nestingly conform to the outer surface of the bone when the imaging of the patient's body structure is carried out. Thus, if a section of the bone is broken (see FIG. 10), the bone-facing surface 24 is designed to compensate or correct the missing bone portion 38. The bone-facing surface 24 will be designed to follow the outer surface of the patient's bone, including the missing bone portion 38, if any. The bone-facing surface 24 is thus adapted to the shape of the bone when the imaging is carried out. The bone-facing surface 24 is free of planar sections, but rather reproduces the corresponding cartilage-free external surface of the bone. In an embodiment, the bone facing surface 24 can include patterns or features formed therein in order to favor the retention of the implant 20. For example and without being limitative, the patterns can include micro-patterns such as micro-grooves formed on the bone facing surface 24 in order to help the retention of the implant 20 on the bone by osteointegration. In another embodiment, other types of patterns or features favoring the retention of the implant 20 on the bone can be used. The patterns can be formed on a section of the bone facing surface 24 or the entire surface thereof.

Figure 9:
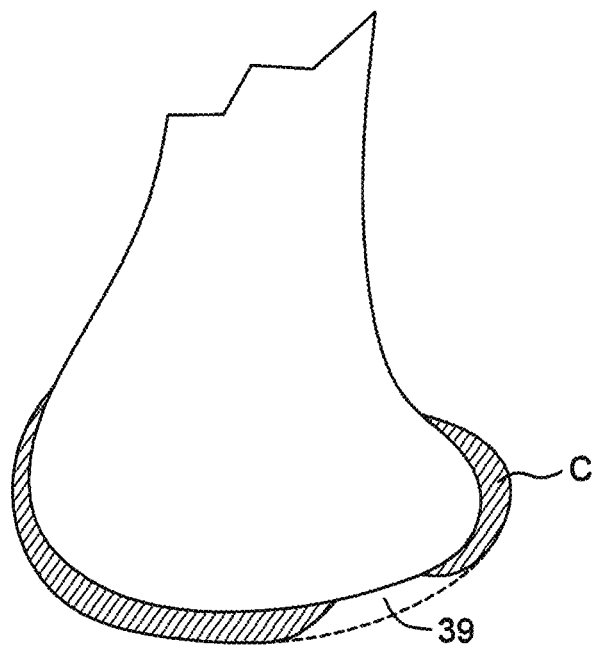
FIG. 9, is a cross sectional schematic representation of a distal femur with a missing cartilage portion.

The shape of the articulating surface 26, opposed to the bone facing surface 24, is typically designed to reproduce the outer shape of the cartilage C, which is superposed to the bone, when the imaging is carried out. Once again, however, if part of the cartilage C covering the bone is missing or broken (see FIGS. 9 and 10), for instance if the patient has osteoarthritis, when the imaging of the patient's body structure is carried out, the articulating surface 26 is designed to compensate or correct the missing cartilage portion 39. Therefore, the thickness of the orthopedic implant can be variable with the orthopedic implant being thicker in sections where the cartilage C and/or the bone is missing or broken. In view of the above, the articulating surface 26 can be a reproduction or a corrected reproduction of the cartilage C covering the bone. In an alternative embodiment, the shape of the articulating surface 26 can also be an offset of the corresponding outer surface of the patient's bone.

Furthermore, the shape of the articulating surface 26 can also be adjusted to correct defaults, for example and without being limitative in the mechanical axis of the patient's leg. Such corrections can be implemented to modify the patient's walking. The correction can be determined by a surgeon according to desired correction parameters. In an alternative embodiment, the articulating surface can also be adjusted in order to increase the thickness between the bone facing surface 24 and the articulating surface 26, uniformly or non-uniformly, for example and without being limitative when the implant 20 is required to have a minimum thickness that is greater than the thickness of the cartilage. Thus, it will be understood that the design of the orthopedic implants can follow two different patterns. First, the shape of the bone-facing surface 24 can follow the shape of the patient's bone, including broken bone sections, when imaging is carried out and the articulating surface 26 can reproduce the shape of the patient's cartilage when imaging is carried out. Second, the shape of the bone-facing surface 24 can follow the shape of the patient's bone, including broken bone sections, when imaging is carried out, and the articulating surface 26 can be based on the shape of the patient's cartilage when imaging is carried out but also compensate for broken or missing cartilage sections and/or modified to correct defaults (corrected reproduction) or reach a minimum thickness.

As shown in FIGS. 1 to 8, the femoral orthopedic implant 20 is self-retaining along at least one axis. In the embodiment shown, the bi-compartmental femoral orthopedic implant 20 has a C-shaped profile, in cross-section, with the free ends defining a restricted passage along the sagittal plane. Thus, when implanted on the distal femur F, the C-shaped profile of the orthopedic implant 20 creates a retaining section 30 which covers a corresponding retaining surface, i.e. the distal femoral condyle, of the distal femur F and thereby restrains the movement of the femoral orthopedic implant 20 along the sagittal plane, i.e. from the anterior side to the posterior side and vice-versa, as well as vertically, i.e. along an axis perpendicular to the transverse plane. As mentioned above, the entire bone-facing surface 24 follows the shape of the bone to which it is secured and is free of planar sections. In the embodiment shown, the retaining section 30 extends upwardly from a section covering the articulation section of the distal femur and covers the femoral condyles, which define at least part of the retaining surface.

The femoral orthopedic implant 20 comprises an articular section designed to cover an articular surface of the distal femur F. The retaining section 30 extends inwardly, towards a center of the distal femur F, upwardly from the section covering the articular surface of the distal femur F.

As can be seen in FIGS. 3 to 8, the bone-facing surface 24 of the bicompartmental orthopedic implant 20 is free of fixation pegs. As will be understood, the configuration of the implant 20, with the retaining section 30, is such that the implant 20 can be stably implanted on the distal femur F without the use of fixation pegs. In the illustrated embodiment of FIGS. 1 and 2, the bicompartmental orthopedic implant 20 is anchored to the distal femur F by two screws 35 (only one is shown) preventing movement of the implant 20 along the unrestrained axis(es). In an alternative embodiment, more or less than two screws can also be used. One skilled in the art will understand that in another alternative embodiment, other known anchoring methods, such as, without being limitative, cementing, can be used for anchoring the implant 20 to the distal femur F. In an embodiment, mechanical fasteners such as screws can be used in combination with adhesive such as cement based adhesive. In another alternative embodiment, osteointegration can also be used to anchor the implant 20.

In order to manufacture the bicompartmental orthopedic implant 20, as mentioned above, an imaging step of the patient's body structure is first carried out and a three-dimensional image reconstruction of the patient's body structure is performed. The image is analysed to determine the retaining surface on the structure of the patient's condyle for the orthopedic implant. The femoral orthopedic implant 20 is subsequently designed and conceived with the bone-facing surface 24 following the shape of the distal femur F of the patient, including broken bone sections 38 and a retaining section 30 conforming to the retaining surface. The articulating surface 26 is designed based on the shape of the patient's cartilage when imaging is carried out. As mentioned above, the articulating surface 26 can also compensate for missing cartilage portions 39 and/or be modified to correct defaults. As mentioned, the femoral orthopedic implant 20 is conceived to be superposed to the distal femur F of the patient in a single position.

When implanting the bicompartmental femoral orthopedic implant 20, the cartilage covering the bone is first removed. The bicompartmental femoral orthopedic implant 20 is subsequently engaged over the distal femur F. In the embodiment shown, a rotation movement is typically carried out for engaging the femoral orthopedic implant 20 over the distal femur, the retaining section 30, being firstly engaged over the corresponding retaining surface of the femur F and the femoral orthopedic implant 20 being subsequently pivoted in place. In the embodiment shown, the retaining section 30 is first engaged over the femoral condyles and, then, the orthopedic implant 20 is pivoted to engage and cover the anterior portion.

Thus, implantation of the orthopedic implant 20 does not require femoral resection. The bone-facing surface 24 follows the shape of the distal femur F when imaging is carried out prior to surgery. Furthermore, the thickness of the orthopedic implant 20 and, thereby, the shape of the articulating surface 26 can be modified in specific sections thereof to correct bone defaults and orthopedic defaults determined by the surgeon. In an embodiment, the modification of the articulating surface is an offset of the shape of the patient's cartilage C when imaging is carried out.

When the surgeon implants the femoral orthopedic implant 20 onto a patient, the design of the femoral implant 20 does not require cutting the anterior cruciate ligaments, as it often occurs with standard off-the-shelf prosthesis.

Figure 11:
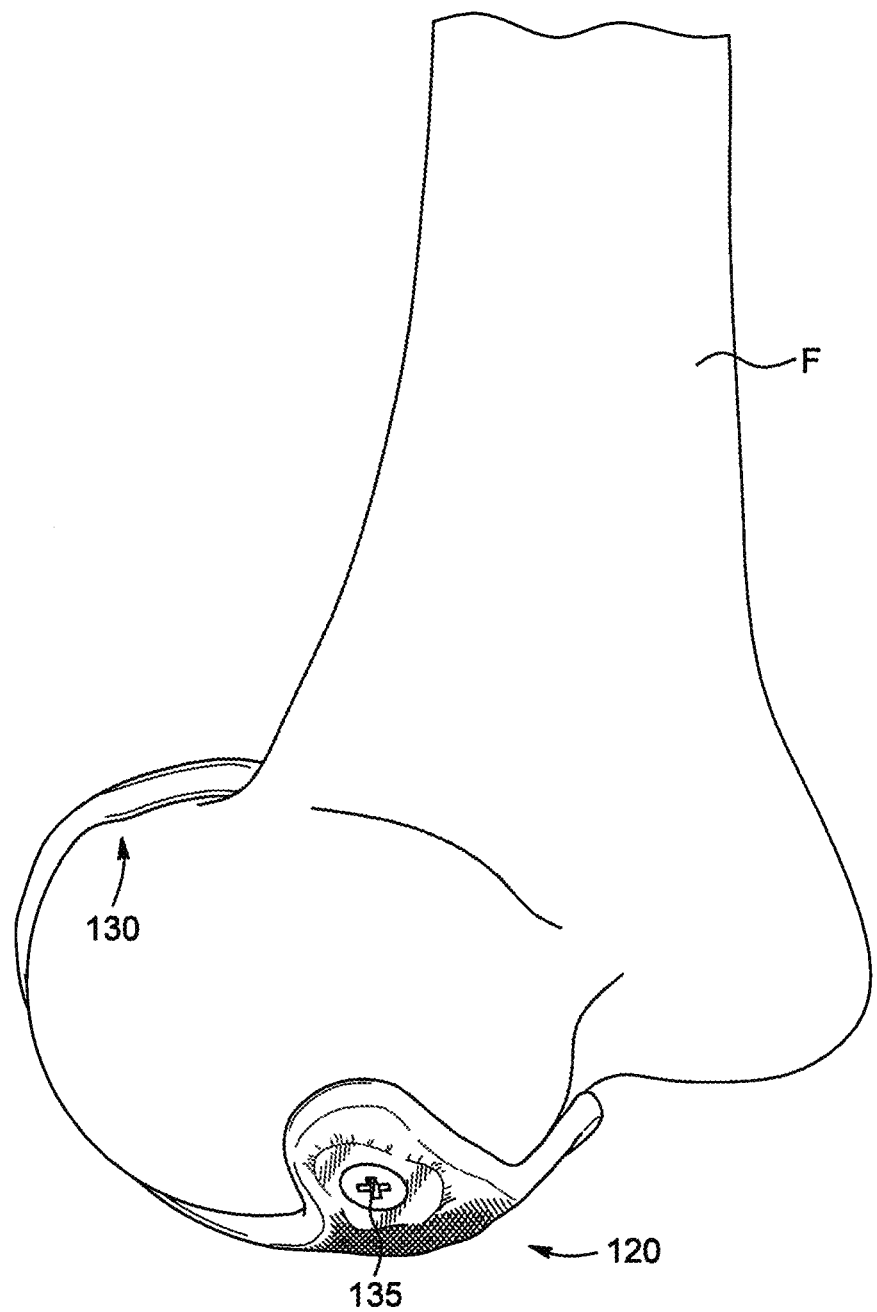
FIG. 11 is a rear perspective view of a unicompartmental femoral orthopedic implant implanted on a non-resected bone surface of a distal femur.
Figure 12:
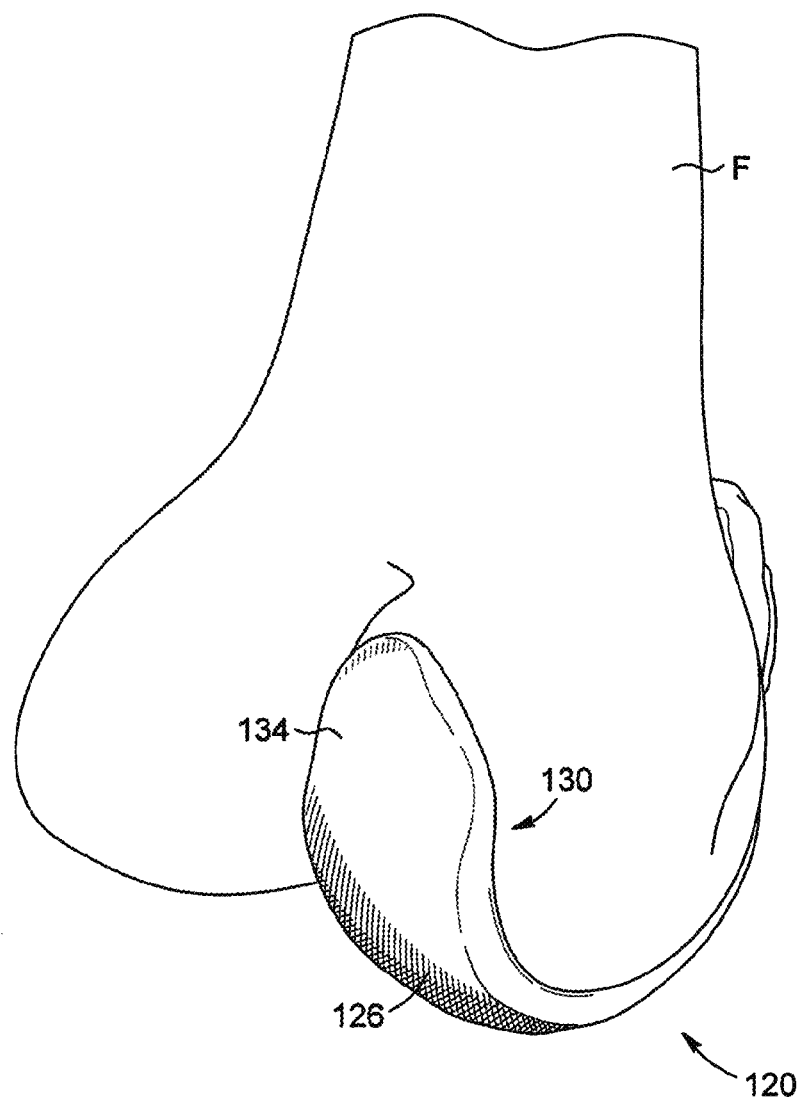
FIG. 12 is a front perspective view of the unicompartmental femoral orthopedic implant shown in FIG. 11, implanted on the non-resected surface of the distal femur.
Figure 13:
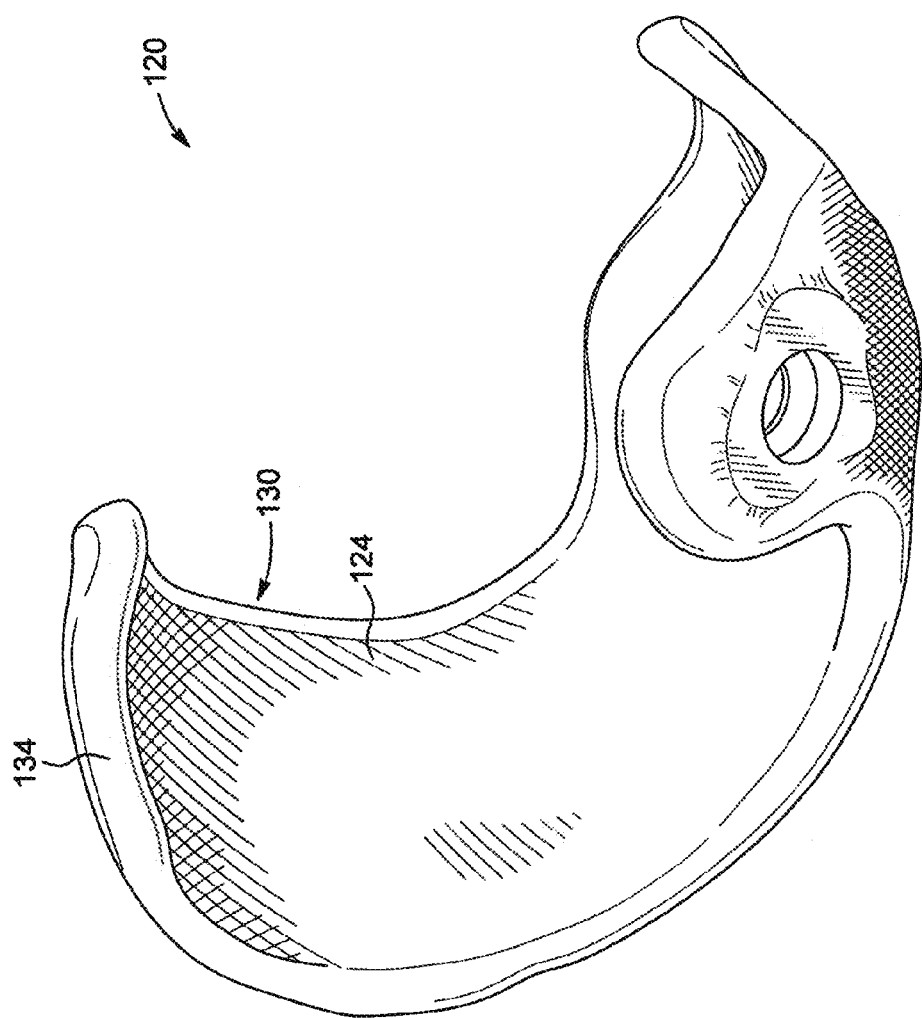
FIG. 13 is a top perspective view of the unicompartmental femoral orthopedic implant shown in FIG. 11, removed from the distal femur.
Figure 14:
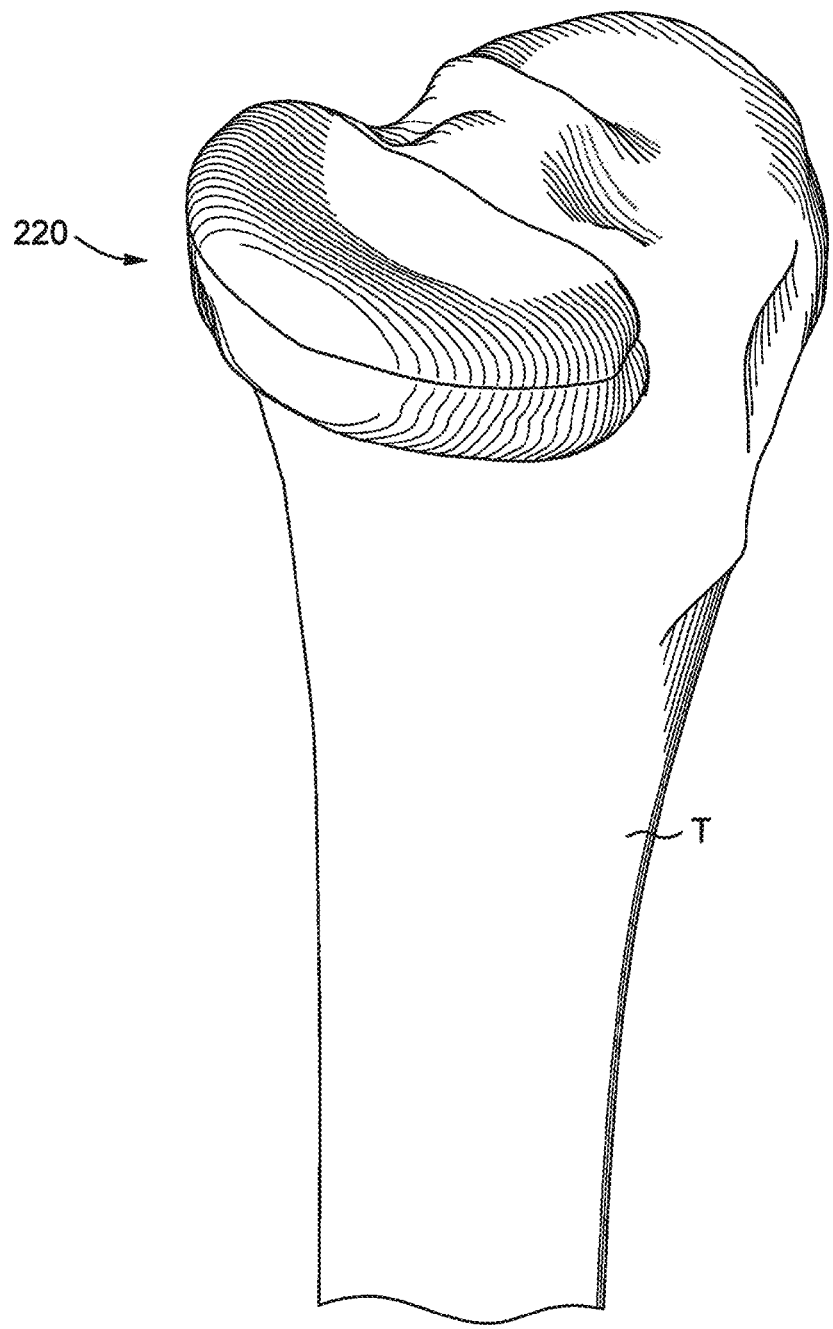
FIG. 14 is a front perspective view of a tibial orthopedic implant implanted on a partially resected medial bone surface of a proximal tibia.

Referring now to FIGS. 11 to 13, there is shown an alternative embodiment of an anatomically adapted orthopedic implant, wherein the features are labelled in the 100 series and which correspond to the reference numerals of the previous embodiment. In accordance with this alternative embodiment, there is provided a unicompartmental femoral orthopedic implant 120 (having a single condyle 134). In this embodiment, the distal surface of the patient's femur F is once again non-resected before implanting the femoral orthopedic implant 120 thereon.

It will be appreciated that the unicompartmental femoral orthopedic implant 120 has similar characteristics as the previously described bicompartmental femoral orthopedic implant 20 regarding the shape of the bone-facing surface 124 and the articulating surface 126 of the body 122. In other words, the bone-facing surface 124 is also configured to be complementary to a portion of a patient's bone surface and nestingly conform thereto when engaged therewith. It can also be designed to compensate or correct a missing or broken bone portion. The articulating surface 126 is also typically designed to reproduce the outer shape of the cartilage, which is superposed to the bone, or represent an offset of the patient's bone when imaging is carried out. It can be designed to compensate or correct missing cartilage portion, or defaults, for example in the mechanical axis of the patient's leg.

Moreover, the unicompartmental femoral orthopedic implant 120 is also self-retaining along at least one axis, as it includes a retaining section 130 which covers a corresponding retaining surface of the distal femur F. Similarly to the bicompartmental orthopedic implant 20, in the embodiment of FIGS. 11 to 13, the implant 120 has a C-shaped profile, in cross-section, with the free ends defining a restricted passage along the sagittal plane and thereby restraining the movement along the sagittal plane, as well as vertically, i.e. along an axis perpendicular to the transverse plane, when implanted. The bone-facing surface 124, including the retaining section 130, is free of planar sections as it reproduces the corresponding cartilage-free external surface of the bone.

Similarly to the bicompartmental orthopedic implant 20, the unicompartmental femoral orthopedic implant 120 is designed to partially cover an articular surface of the distal femur F. The retaining section 130 extends inwardly, towards a center of the distal femur F, upwardly from the section covering the articular surface of the distal femur F.

The bone-facing surface 124 of the unicompartmental femoral orthopedic implant 120 is also free of fixation pegs and the implant 120 can be anchored to the distal femur F by the above described means, such as, for example, a screw 135.

One skilled in the art will understand that, even though the unicompartmental femoral orthopedic implant 120 shown in FIGS. 11 to 13, is designed to be implanted on the medial femoral condyle of a patient, in an alternative embodiment, it can be designed to be implanted on a lateral femoral condyle of a patient. In another alternative embodiment, unicompartmental femoral orthopedic implants 120 can be implanted on the medial femoral condyle and the lateral femoral condyle to form a bicompartmental (or total) implant where the compartments are not joined to one another.

In another embodiment (not shown), the bicompartmental femoral orthopedic implant can include two implant components configured in an adjacent configuration, each one of the implant components covering a respective one of the medial femoral condyle and the lateral femoral condyle. In one embodiment, the two implant components can be configured in an adjacent and contiguous configuration. In another configuration, the two implant components can be configured in an adjacent and partially overlapping configuration wherein an edge region of one of the two implant components at least partially overlaps the edge region of the other one of the two implant components. In an embodiment, the two implant components can be secured together and to the bone with one or more fastener having a head, such as a suitable screw. The head can be designed to at least partially abut on both implant components, with the fastener extending through the bone. The implant components can include a recess defined in their articular surface in which the head can be received. Thus, an upper surface of the head of the fastener can be substantially leveled with the articular surface of the two implant components. Moreover, a portion of the two implant components extends between the fastener head and the bone, thereby securing the two implant components to the bone.

Referring now to FIGS. 14 to 24, there is shown another alternative embodiment of an anatomically adapted orthopedic implant, wherein the features are labelled in the 200 series and which correspond to the reference numerals of the previous embodiments.

In accordance with this alternative embodiment, there is provided a tibial orthopedic implant 220 for a tibial knee joint. The tibial orthopedic implant 220 is implanted on a partially resected bone surface (or implant region) of a medial section of a proximal tibia T. As will be described in more details below, the proximal surface of the patient's tibia T is partially resected prior to the implantation of the tibial orthopedic implant 220 thereon.

The tibial orthopedic implant 220 comprises a body 222 with a bone-facing surface 224 (or contact surface) and an articulating surface 226 (or receiving surface), opposed to the bone-facing surface 224.

In an embodiment, the body 222 includes a base plate 240 and an articulation plate 242 connectable to the base plate 240. The base plate 240 includes the bone-facing surface 224 (FIG. 20) and an opposed articulation plate engagement surface 225. The articulation plate 242 includes the articulating surface 226 and an opposed base plate engagement surface 227. The articulation plate engagement surface 225 of the base plate 240 and the base plate engagement surface 227 of the articulation plate 242 are complementary in shape to allow the articulation plate 242 to be secured to the base plate 240, following the implantation of the base plate 240 on the tibia T of the patient. For example and without being limitative, the articulation plate engagement surface 225 of the base plate 240 and the base plate engagement surface 227 of the articulation plate 242 can comprise complementary male-female assemblies allowing the secure engagement of the articulation plate 242 to the base plate 240.

In an embodiment, the base plate 240 is made of a cobalt-chromium alloy while the articulation plate 242 is made of biocompatible plastic such as high-molecular-weight polyethylene (HMWPE), ultra-high-molecular-weight polyethylene (UHMWPE), Polyether ether ketone (PEEK), or the like. One skilled in the art will understand that, in an alternative embodiment, the body 222 of the tibial orthopedic implant 220 can be a single piece where the base plate 240 and the articulation plate 242 are joined to form an integral component.

The base plate 240 also includes an outer side surface 229 forming the exposed outer face of the implant 220. The outer side surface 229 extends between the bone-facing surface 224 and the articulation plate engagement surface 225, thereby connecting the two together. The side surface 229 has a side surface morphology, which is the form and structure of the side surface 229. The side surface morphology matches the outer morphology of the corresponding surface of a tibial portion which was removed from the tibia during the resection thereof. The term "matches" or "matching" is used herein to describe the relationship between morphologies and refers to the similarity between these surface profiles, in that both morphologies substantially correspond. This is better appreciated by explaining how the side surface morphology may be generated, according to an embodiment.

In an embodiment, prior to inserting the implant 220, a scan of the portion of the tibia T to be resected is performed. The scan provides information (data) regarding the contour, shape, and profile of the outer surface of the Tibia T which the implant 220 is intended to replace. This information can be used to design the side surface morphology of the side surface 229 (as well as other exterior surfaces) such that the implant 229 can be considered custom designed to the specific patient in which it will be implanted. When the implant 220 is manufactured, the side surface morphology can be applied to the side surface 229, thereby producing a patient-specific implant 220. It will be appreciated that such a side surface morphology helps to mimic the resected portion of the Tibia T, and can further help integration of the implant 220 with the bone. The matching morphologies also help the implant 220 to better mate with the bone, thereby allowing for better cooperation between the implant 220 and the bone.

In an embodiment, the bone-facing surface 224 of the base plate 240 is once again configured to be complementary to a portion of a patient's bone surface and nestingly conform thereto when engaged therewith. However, given that the tibial orthopedic implant 220 is designed to be implanted on a partially resected tibia T, sections of the bone-facing surface 224 are configured to match a resected bone section (or application surface of the implant region). Once again, in an embodiment, the bone facing surface 224 can include patterns such as the one described above in reference to the femoral orthopedic implant. Exemplary embodiments of such patterns are discussed below with reference to FIGS. 26B to 26D.

In the illustrated embodiment, and as better seen in FIGS. 15, 17 and 20 to 22, the bone-facing surface 224 has a transverse planar section 250 extending along a transverse axis defined by a medial plateau 254 (application surface) formed in the proximal tibia T by the partial resection thereof. The transverse planar section 250 is configured to be juxtaposed and fit onto the medial plateau 254. The bone-facing surface 224 also has a sagittal planar section 252 extending along a sagittal axis defined by a medial wall 256 also formed in the proximal tibia T by the partial resection thereof. The sagittal planar section 252 is configured to be juxtaposed and fit onto the medial wall 256. The angle between the transverse planar section 250 and the sagittal planar section 252 therefore corresponds to the angle formed between the medial plateau 254 and the medial wall 256, in order to provide a precise fit of the base plate 240 on the partially resected proximal tibia T.

In an embodiment, the angle between the medial plateau 254 and the medial wall 256 is an acute angle, the medial wall 256 being vertically inclined towards the medial plateau 254. In such an embodiment, the angle between the transverse planar section 250 and the sagittal planar section 252 is therefore a corresponding acute angle. In an embodiment, the angle between the transverse planar section 250 and the sagittal planar section 252 ranges between 75 and 89 degrees. As will be described in more details below, in an alternative embodiment the medial plateau 254 and the medial wall 256 can be perpendicular and thereby form a right angle. In such an embodiment, the angle between the transverse planar section 250 and the sagittal planar section 252 would be a corresponding right angle. In another alternative embodiment, the medial plateau 254 and the medial wall 256 can form an obtuse angle, for example and without being limitative due to physiological restrictions of the patient for performing the resection, the angle between the transverse planar section 250 and the sagittal planar section 252 being a corresponding obtuse angle.

Still referring to FIGS. 15, 17 and 20 to 22, the base plate 240, further includes a substantially U-shaped flange 258 (or attachment flange) extending downwardly and inwardly from the periphery of the transverse planar section 250. In an embodiment, the flange 258 covers the periphery of the transverse planar section 250, outside of the medial wall 256. One skilled in the art would however understand that, in an alternative embodiment, the flange 258 can cover only a portion of the periphery of the transverse planar section 250 outside of the medial wall 256. In an embodiment, the flange 258 can include a plurality of spaced-apart flange sections defining together a substantially U-shaped profile. The internal surface 260 (or abutment surface) of the flange 258 is patient specific and is part of the bone-facing surface 224 as it is configured to mate with the corresponding portion of the patient's bone surface.

As can be seen in FIGS. 14 to 17, the internal surface 260 of the flange 258 matches the contour of the proximal tibia T of the patient, around the resected medial plateau 254. Therefore, the shape of the internal surface 260 of the flange 258 varies in accordance with the shape of the patient's bone.

Therefore, similarly to the above described implants, the design of the tibial orthopedic implant 220 is based on an image of at least a portion of the body structure of the patient, including the tibia T.

The bone-facing surface 224 is designed with the flange 258 having an internal surface 260 fitting the cartilage-free outer surface of the bone when the imaging of the patient body structure is carried out. The transverse planar section 250 and the sagittal planar section 252 are designed to fit the resected portions of the bone subsequently to a partial resection thereof.

Figure 15:
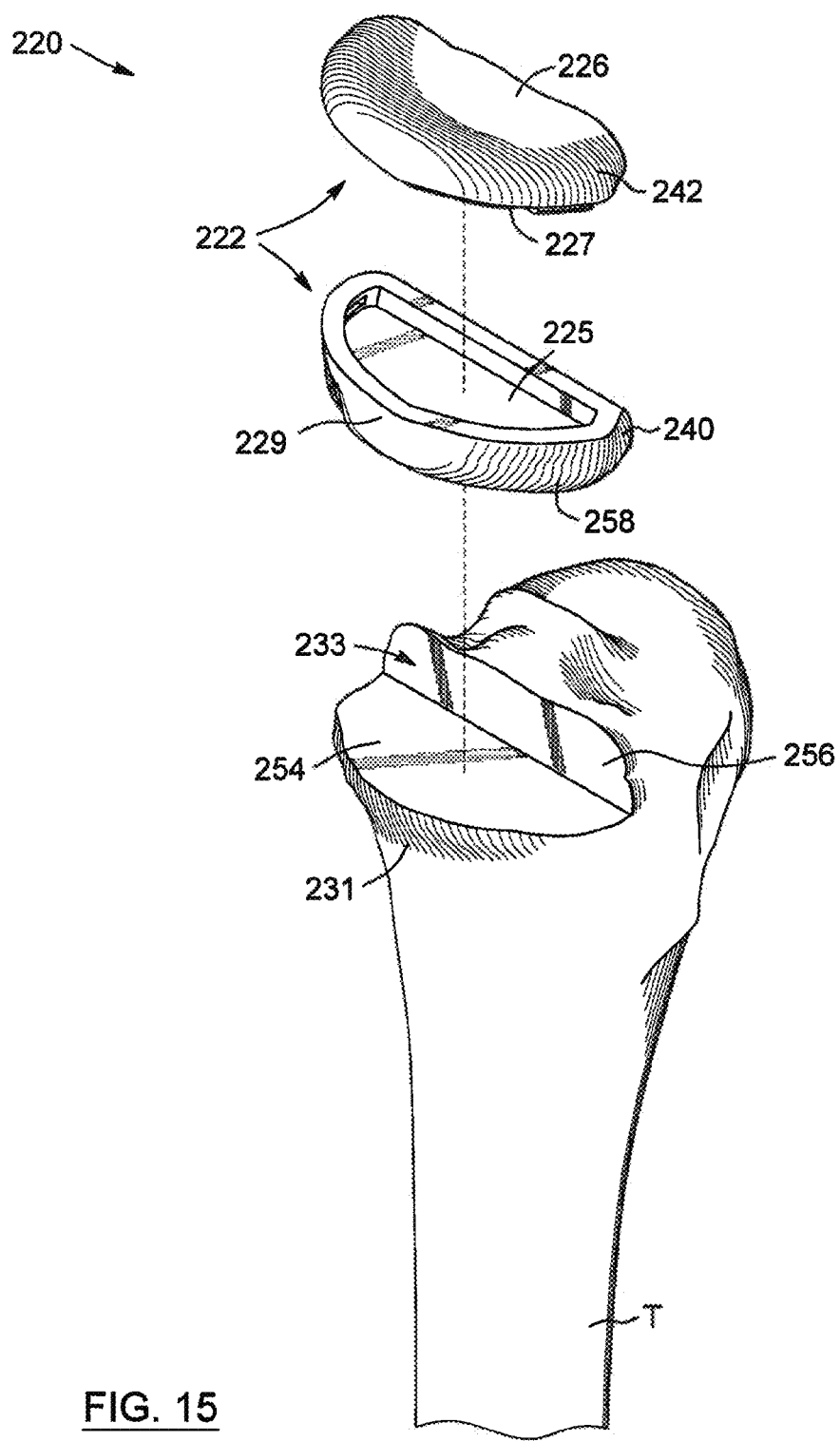
FIG. 15 is a front exploded view of the tibial orthopedic implant and partially resected proximal tibia of FIG. 14.
Figure 16:
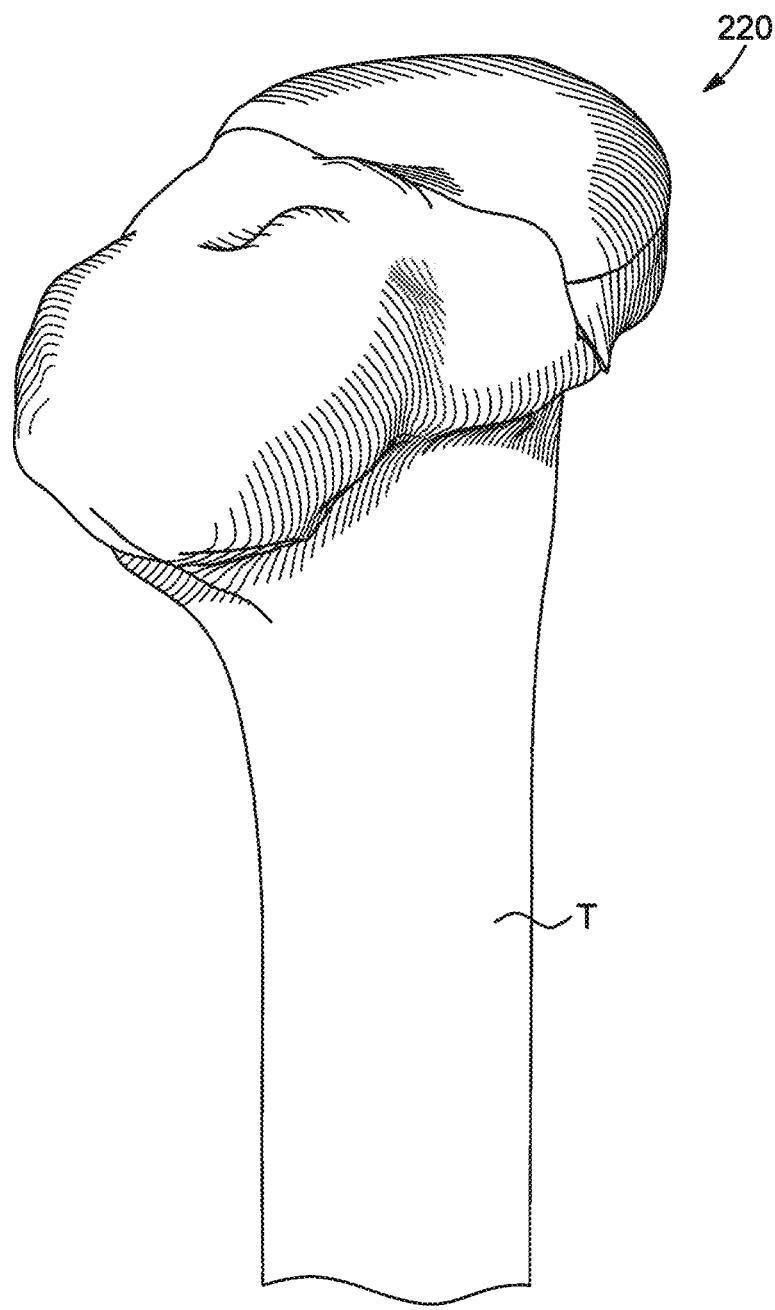
FIG. 16 is a rear perspective view of the tibial orthopedic implant shown in FIG. 14, implanted on the partially resected medial bone surface of the proximal tibia.
Figure 17:
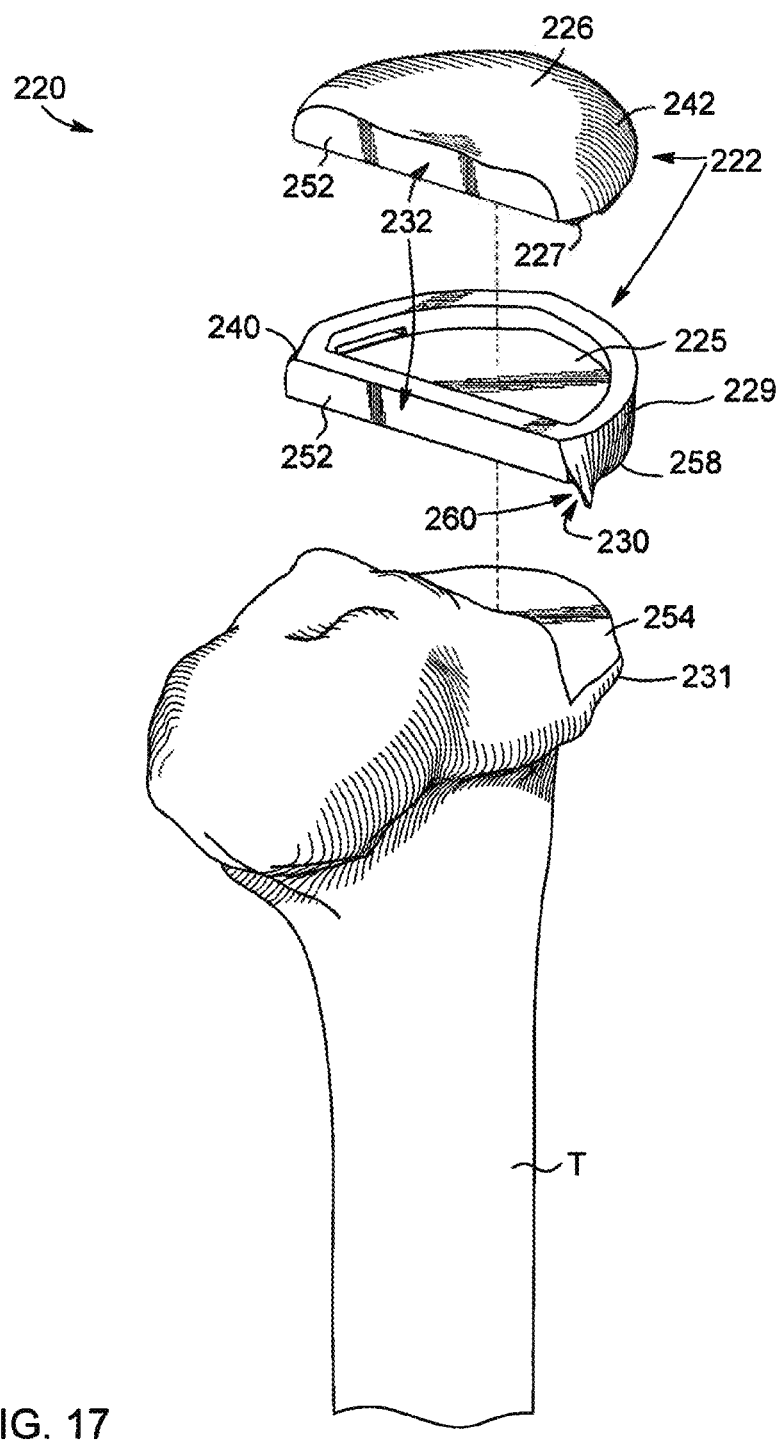
FIG. 17 is a rear exploded view of the tibial orthopedic implant and partially resected proximal tibia of FIG. 16.
Figure 18:
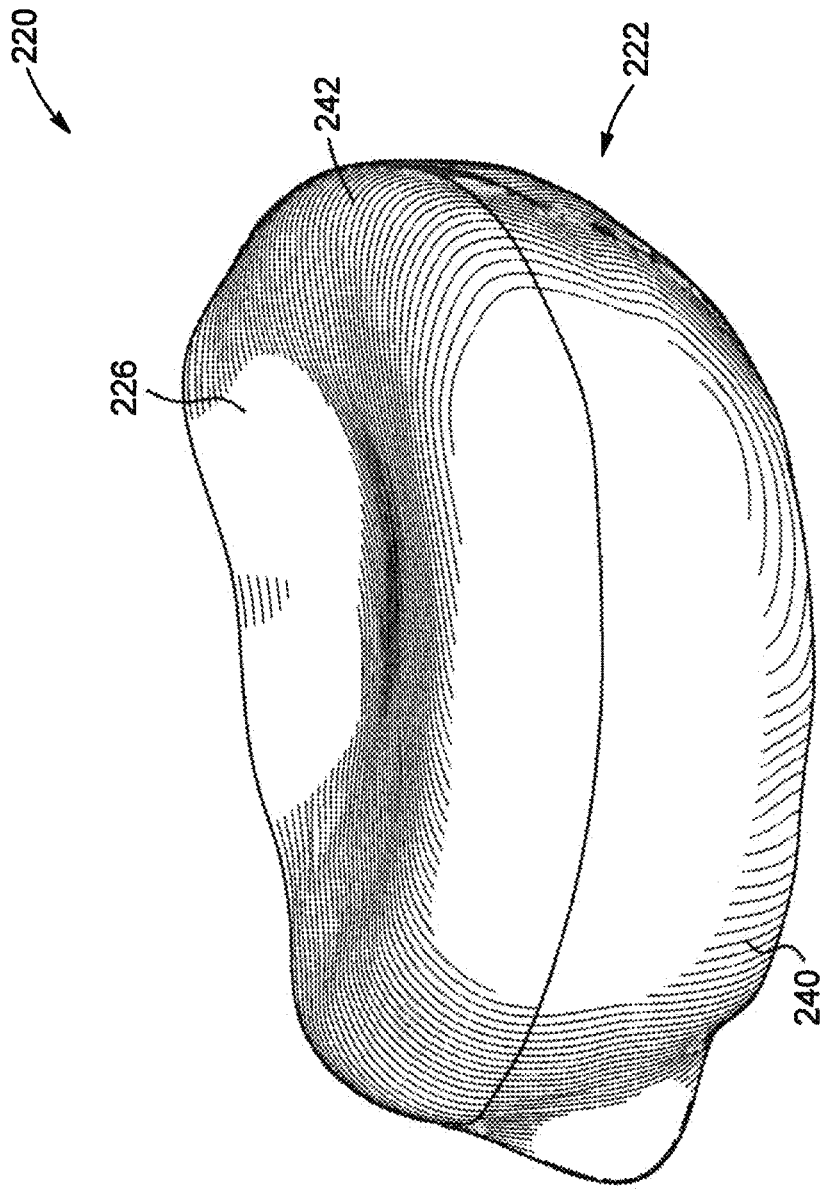
FIG. 18 is a top perspective view of the tibial orthopedic implant shown in FIG. 14, removed from the proximal tibia.
Figure 19:
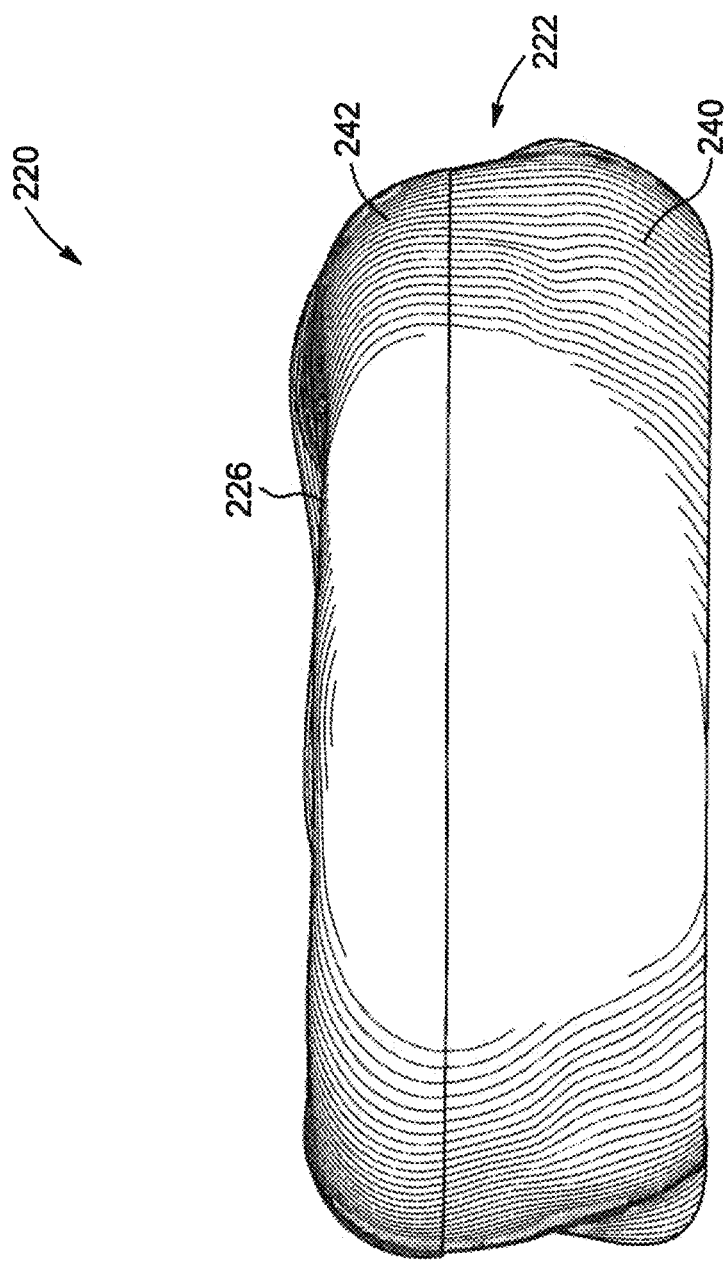
FIG. 19 is a side elevation view of the tibial orthopedic implant shown in FIG. 18.

As shown more clearly in FIGS. 15 and 17, the tibial orthopedic implant 220 is once again self-retaining along at least one axis. In the embodiment shown, the movement of the tibial orthopedic implant 220 is restrained along the sagittal plane, i.e. along an axis extending from the anterior side to the posterior side and vice-versa, as well as vertically, i.e. along an axis extending perpendicular to the transverse plane, when implanted. The restriction of the movement of the tibial orthopedic implant 220 results from the combination of the flange 258 projecting inwardly towards the corresponding section of the tibia T (thereby forming a first retaining section 230 covering a first retaining surface 231 of the tibia T) and the acute angle between the transverse planar section 250 and the sagittal planar section 252 matching the acute angle between the medial plateau 254 and the medial wall 256 (thereby forming a second retaining section 232 covering a second retaining surface 233 of the tibia T). The first retaining section 230 restrains movement of the orthopedic implant 220 along the sagittal plane as well as vertically. The second retaining section 232 restrains movement of the orthopedic implant 220 vertically only.

One skilled in the art will therefore understand that, in an alternative embodiment, the above-described restriction of the movement of the tibial orthopedic implant 220 along the sagittal plane as well as vertically can be achieved by providing the first retaining section 230 formed by the flange 258 projecting inwardly towards the corresponding section of the tibia T only. In other words, the second retaining section 232 provided by the medial wall 256 and resulting from the acute angle between the transverse planar section 250 and the sagittal planar section 252 matching the acute angle between the medial plateau 254 and the medial wall 256 provides optional increased support to restrain the movement of the tibial orthopedic implant 220 vertically.

The tibial orthopedic implant 220 is designed to partially cover an articular surface of the proximal tibia T. For the tibial orthopedic implant 220, the articular surface is resected and includes the medial plateau 254. The first retaining section 230 extends inwardly, from the peripheral edge of the transverse planar section 250, towards a center of the proximal tibia T, downwardly from the transverse planar section 250 covering the articular surface of the proximal tibia T.

The bone-facing surface 224 of the first retaining section 230 is free of planar sections, but rather reproduces the corresponding cartilage-free external surface of the bone.

Figure 20:
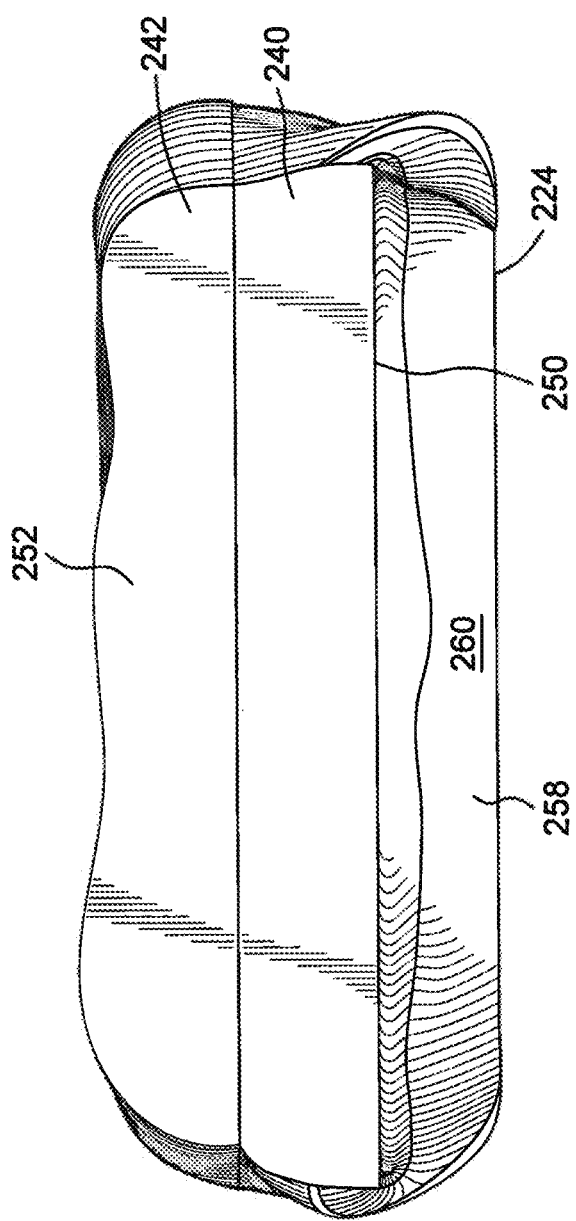
FIG. 20 is a side elevation view of the tibial orthopedic implant shown in FIG. 18, and showing the opposed side of FIG. 19.
Figure 21:
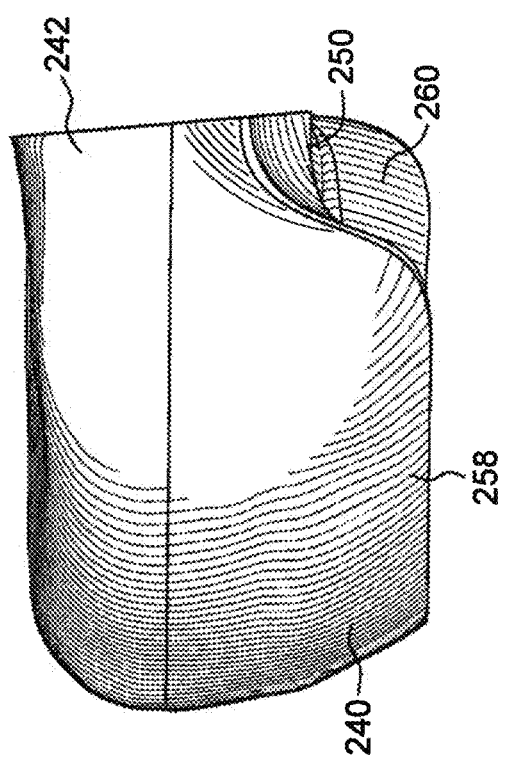
FIG. 21 is a front elevation view of the tibial orthopedic implant shown in FIG. 18.
Figure 22:
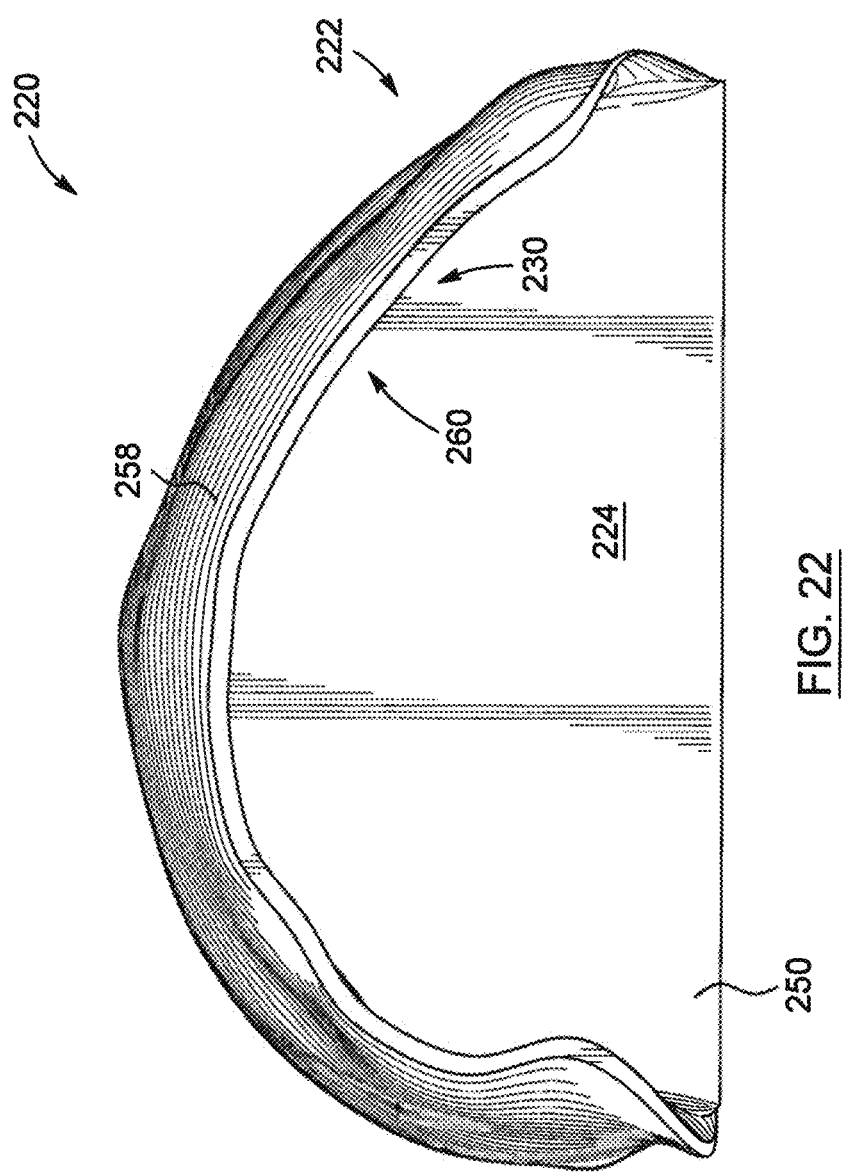
FIG. 22 is a bottom plan view of the tibial orthopedic implant shown in FIG. 18.
Figure 23:
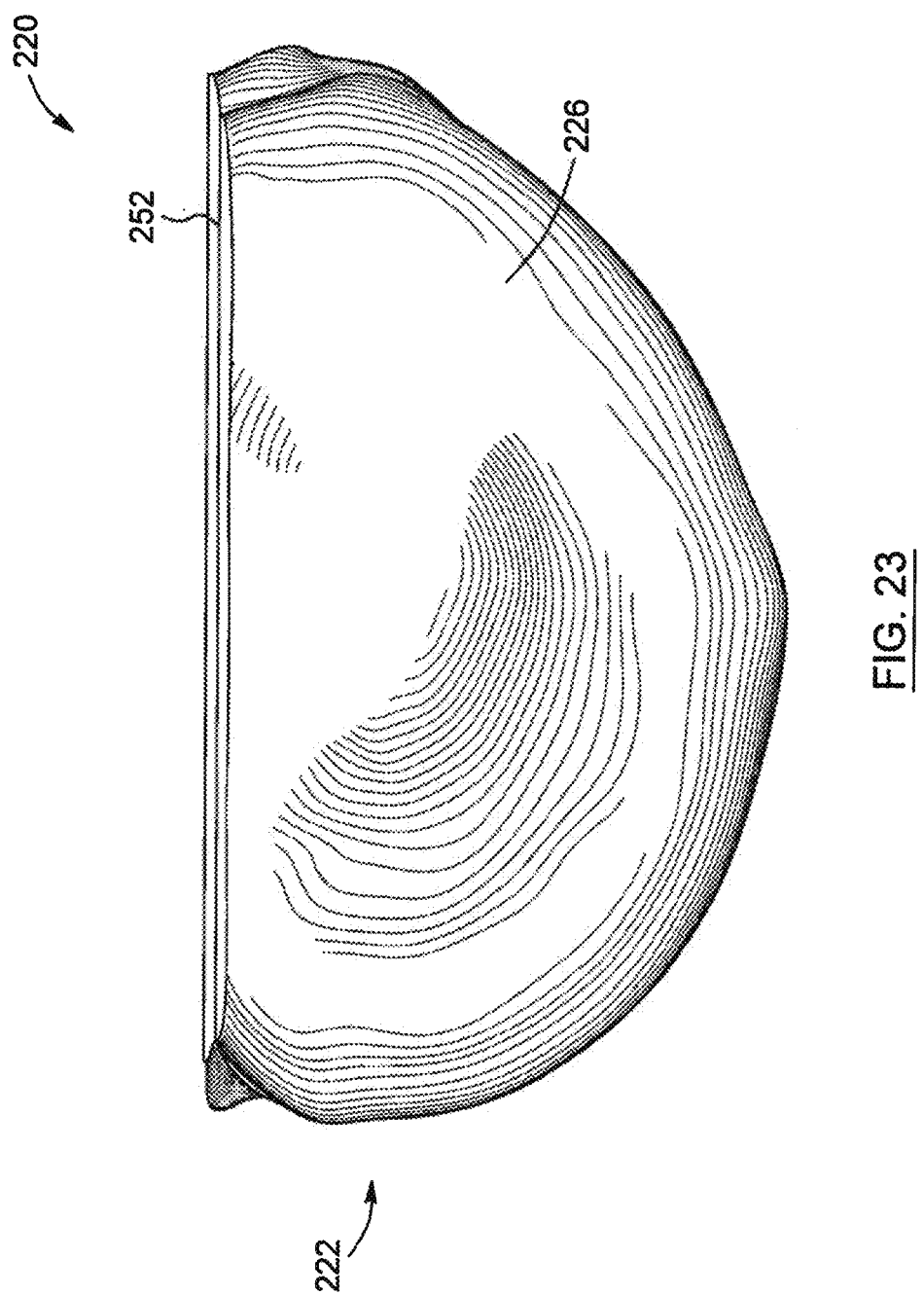
FIG. 23 is a top plan view of the tibial orthopedic implant shown in FIG. 18.

As can be seen in FIGS. 20 to 22, the bone-facing surface 224 of the tibial orthopedic implant 220 is once again free of fixation pegs and directly matches the corresponding faces of the resected and non-resected sections of the proximal tibia T.

Figure 24:
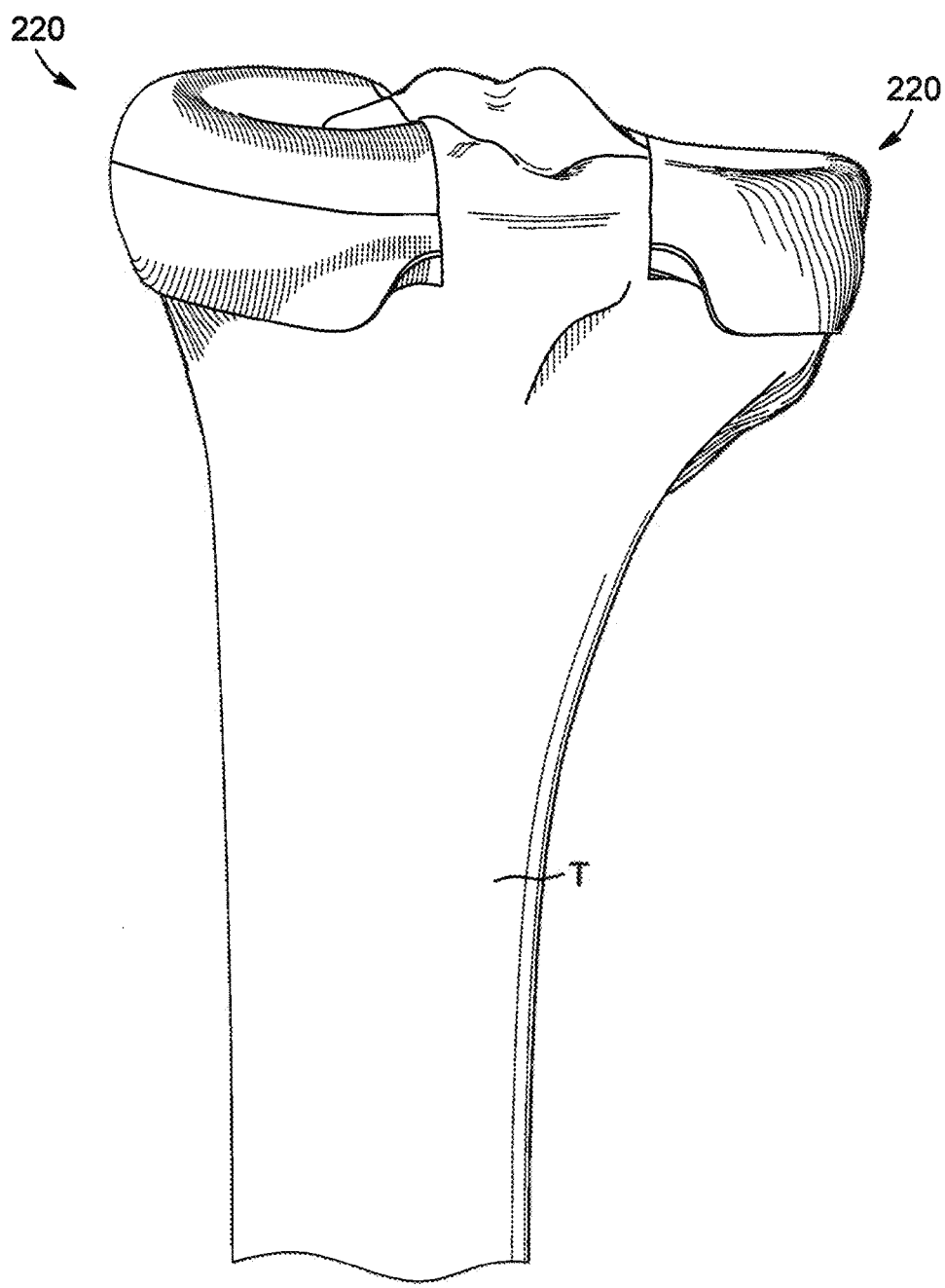
FIG. 24 is a front elevation view of a proximal tibia including two tibial orthopedic implants in accordance with an embodiment.
Figure 25:
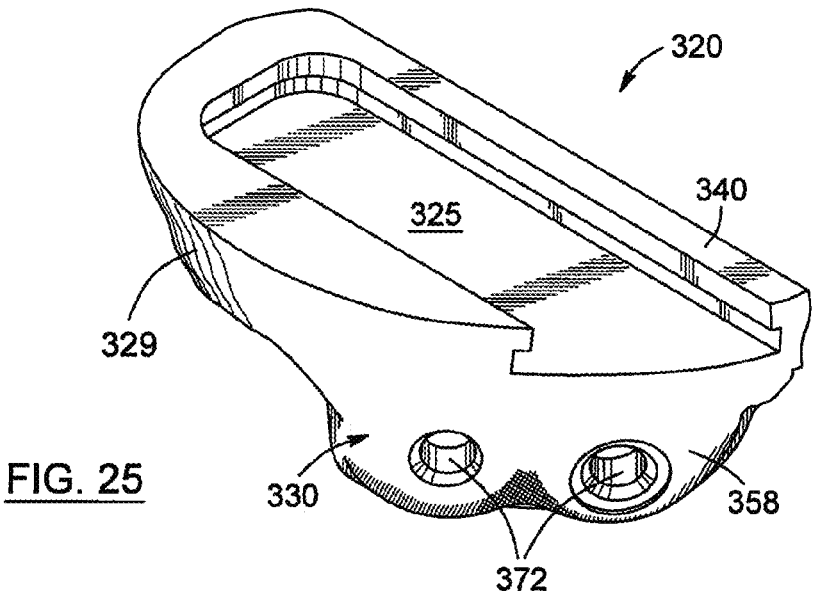
FIG. 25 is a top perspective view of a base plate of the tibial orthopedic implant in accordance with another embodiment.

Now referring to FIG. 24, one skilled in the art will understand that even though the above description of FIGS. 14 to 23 referred to a single tibial orthopedic implant 220 for a medial section of a proximal tibia T, in an embodiment where a bicompartmental (or total) knee surgery is performed, tibial orthopedic implants 220 can be provided on the medial and lateral sections of the proximal tibia T of a patient. Moreover, in an alternative embodiment (not shown), a single tibial orthopedic implant 220 for a lateral section of a proximal tibia T, can also be provided.

Referring now to FIGS. 25 to 29, there is shown another alternative embodiment of an anatomically adapted orthopedic implant and, more particularly, a tibial orthopedic implant 320 for a tibial knee joint, wherein the features are labelled in the 300 series and which correspond to the reference numerals of the previous embodiments. As for the above described tibial orthopedic implant 220, the tibial orthopedic implant 320 is conceived to be implanted on a partially resected bone surface of a medial section of a proximal tibia T. However, the shape and configuration of the retaining sections and the shape and configuration of the articulation plate engagement surface 325 of the base plate 340 are different than those of the above described tibial orthopedic implant 220.

Similarly to the above described implants, the design of the tibial orthopedic implant 320 is based on an image of at least a portion of the body structure of the patient, including the tibia T.

The tibial orthopedic implant 320 comprises a base plate 340 and an articulation plate. In the figures, solely the base plate 340 of the body 322 is shown. The base plate 340 is designed to be engageable with the articulation plate (not shown). The base plate 340 includes the bone-facing surface 324 (FIG. 26) and an opposed articulation plate engagement surface 325. The articulation plate engagement surface 325 of the base plate 340 is designed to be complementary in shape to the base plate engagement surface of the articulation plate.

In an embodiment, the bone-facing surface 324 of the base plate 340 is once again configured to be complementary to a portion of a patient's bone surface and nestingly conform thereto, when engaged therewith. More particularly, the bone-facing surface 324 of the tibial orthopedic implant 320 comprises sections configured to match a resected bone section and sections configured to match an unresected bone section. Once again, in an embodiment, the bone facing surface 324 can include patterns such as the one described above in reference to the femoral orthopedic implant.

As the bone-facing surface 224, the bone-facing surface 324 has a transverse planar section 350 configured to be juxtaposed and fit onto the medial plateau of the resected tibia T and a sagittal planar section 352 configured to be juxtaposed and fit onto the medial wall 356 of the resected tibia T.

The base plate 340 includes a substantially U-shaped flange 358 extending downwardly and inwardly from the periphery of the transverse planar section 350. In the embodiment shown, the flange 358 covers only a portion of the periphery of the transverse planar section 350 outside of the medial wall 356. In another embodiment, the flange 358 can cover the entire periphery of the transverse planar section 350, outside of the medial wall 356. The internal surface 360 of the flange 358 is patient specific and is part of the bone-facing surface 324 as it is configured to mate with the corresponding portion of the patient's bone surface. Thus, the internal surface 360 of the flange 358 matches entirely and nestingly conforms to the contour of the proximal tibia T of the patient, around the resected medial plateau 354. Therefore, the shape of the internal surface 360 of the flange 358 varies in accordance with the shape of the patient's bone and fits the cartilage-free outer surface of the bone when the imaging of the patient body structure is carried out.

The tibial orthopedic implant 320 is once again self-retaining along at least one axis. The movement of the tibial orthopedic implant 320 is restrained partially along the sagittal plane, i.e. from the anterior side to the posterior side and vice-versa, as well as vertically. As for the tibial orthopedic implant 220, the restriction of the movement of the tibial orthopedic implant 320 results from the combination of the flange 358 projecting inwardly towards the corresponding section of the tibia T (thereby forming a first retaining section 330 covering a first retaining surface of the tibia T) and the acute angle between the transverse planar section 350 and the sagittal planar section 352 matching the acute angle between the medial plateau 354 and the medial wall 356 (thereby forming a second retaining section 332 covering a second retaining surface 333 of the tibia T). The first retaining section 330 restrains movement of the orthopedic implant 320 partially along the sagittal plane as well as vertically. The second retaining section 332 restrains movement of the orthopedic implant 320 vertically only.

The bone-facing surface 324 of the first retaining section 330 is free of planar sections, as it reproduces the corresponding cartilage-free external surface of the bone.

Similarly to the above described tibial orthopedic implant 220, the tibial orthopedic implant 320 is designed to partially cover a resected articular surface of the proximal tibia T, including the medial plateau. The retaining section 330 extends inwardly, from the peripheral edge of transverse planar section 350, towards a center of the proximal tibia T, downwardly from the transverse planar section 350 covering the articular surface of the proximal tibia T.

Figure 26:
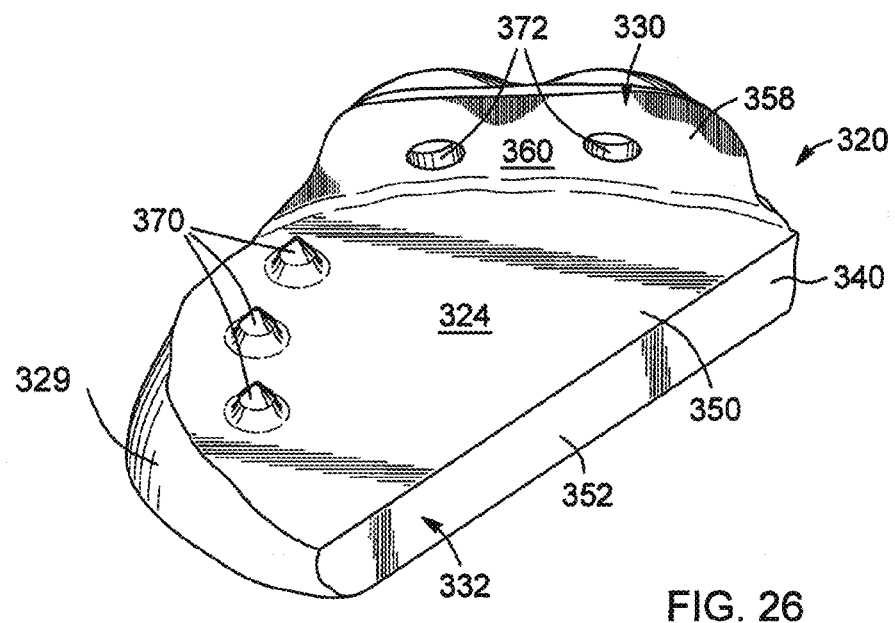
FIG. 26 is a bottom perspective view of the base plate of the tibial orthopedic implant shown in FIG. 25.
Figure 26A:
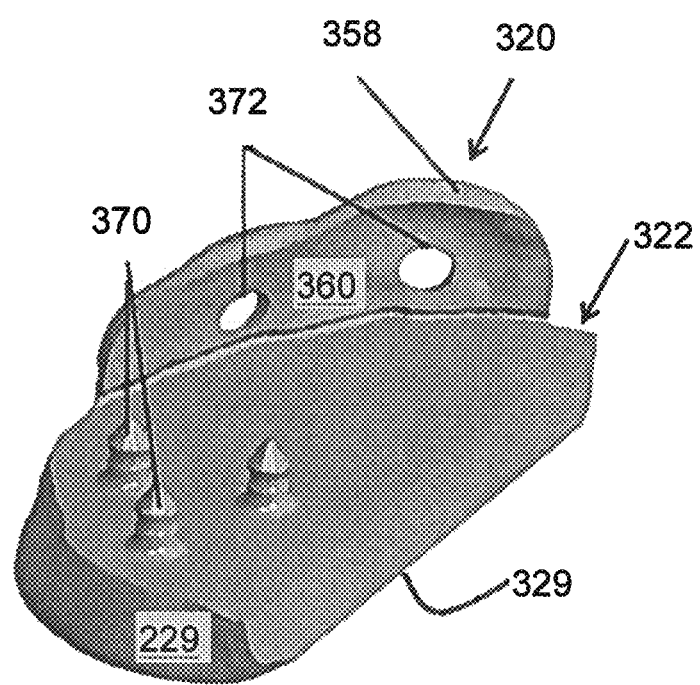
FIG. 26A is a bottom perspective view of the base plate of the tibial orthopedic implant shown in FIG. 26 including fixation pegs according to an embodiment.
Figure 27:
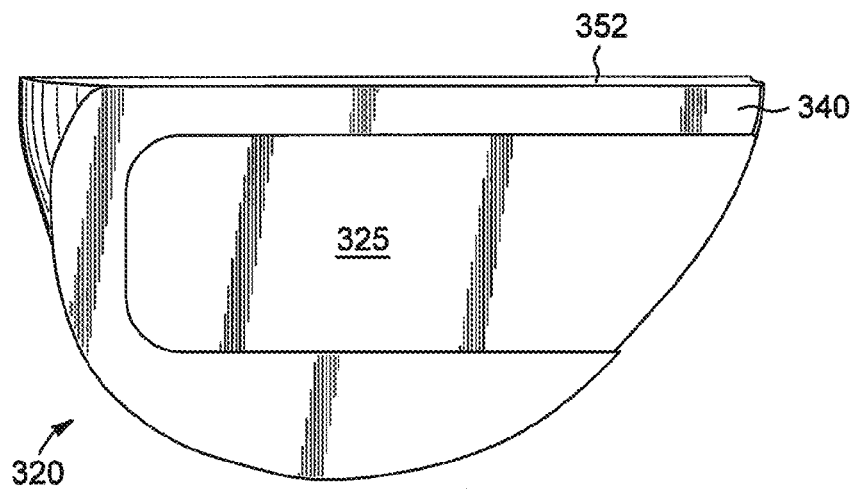
FIG. 27 is a top plan view of the base plate of the tibial orthopedic implant shown in FIG. 25.
Figure 28:
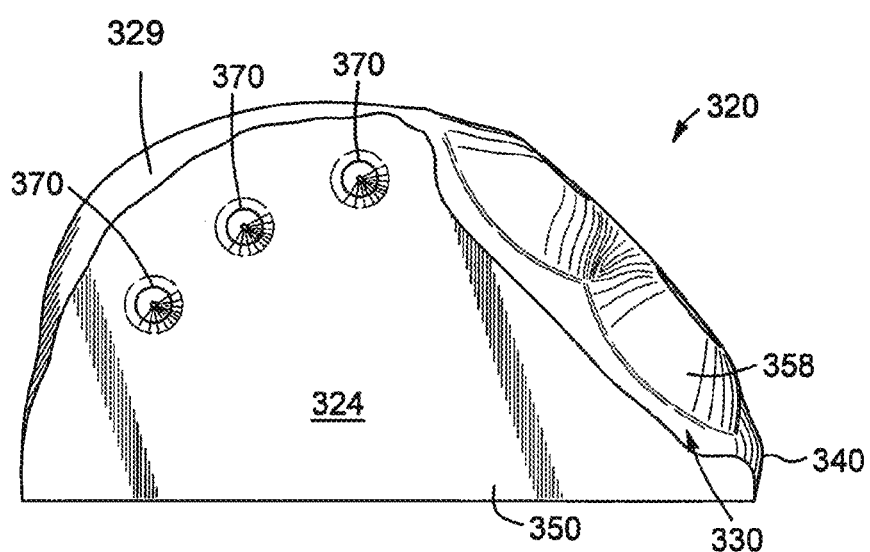
FIG. 28 is a bottom plan view of the base plate of the tibial orthopedic implant shown in FIG. 25.
Figure 29:
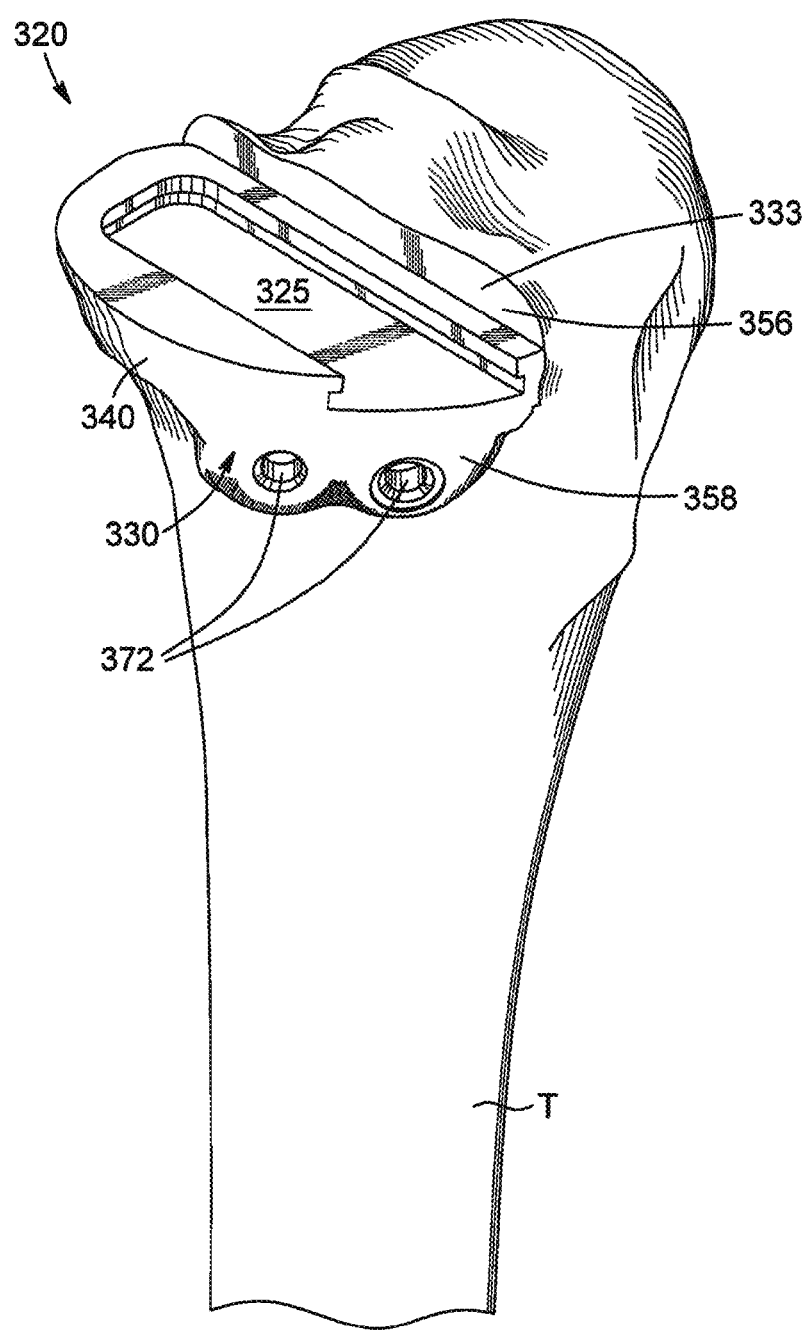
FIG. 29 is a front perspective view of the base plate of the tibial orthopedic implant shown in FIG. 25, implanted on the partially resected medial bone surface of the proximal tibia.

As can be seen in FIGS. 26 and 26A, in an embodiment, the bone-facing surface 324 of the tibial orthopedic implant 320 also comprises a plurality of fixation pegs 370 (or engagement members) insertable in the tibia through the medial plateau 354. The fixation pegs 370 penetrate into the medial plateau 354 of the resected tibia when the bone-facing surface 324 is abutted thereagainst. In so doing, the fixation pegs 370 help to secure the implant 320, to the medial plateau 354. Each fixation peg 370 extends away from the bone-facing surface 324 along a longitudinal direction aligned with an axis of the tibia T, when the orthopedic implant 320 is implanted thereon. The fixation pegs 370 are spaced apart from one another, and can be positioned on a portion of the bone-facing surface 324 that is opposite the flange 358. Such a positioning of the fixation pegs 370 can provide additional stability to the implant 320 away from the flange 358. The fixation pegs 370 can have different shapes. In FIG. 26, for example, each fixation peg 370 has a first substantially cylindrical portion extending away from the bone-facing surface 324 which is followed by a conical portion. One skilled in the art will understand that other shapes for the fixation pegs 370 are also within the scope of the present disclosure. For example, and as shown in FIG. 26A, each of the three fixation pegs 370 can have a ribbed cylindrical portion followed by a conical portion.

In some embodiments, examples of which are provided in FIGS. 26B to 26D, the bone-facing surface 324 can also include a pattern with one or more projections projecting away from the bone-facing surface 324, along a direction aligned with the axis of the tibia T, when the orthopedic implant 320 is implanted thereon. Alternatively, the projections can be considered to project inwardly from the bone-facing surface 324. Such projections can be carved into the surface to create a pattern on the bone-facing surface 324. In either case, the pattern can occupy some portion, or all, of the bone-facing surface 324, and provides a medium for bone ingrowth which helps to secure the body 322 (and thus the implant 320) to the bone tissue to which it is attached. In so doing, the pattern encourages osseointegration, which refers to the direct structural and functional connection between living bone tissue and the bone-facing surface 324 of the load-bearing artificial implant 320. The pattern can be a mono-construction and thus integrally formed with the implant 320, or can be added to the bone-facing surface 324 separately. The pattern can also be combined with one or more of the previously-discussed fixation pegs 370. The pattern can therefore assume many different configurations in order to provide such functionality. Three possible configurations for the pattern will now be discussed, and it will be appreciated that many other possible configurations are within the scope of the present disclosure.

FIG. 26B shows a pattern 374 having multiple projections 376 resulting from a portion of the bone-facing surface 324 having been carved away. The projections 376 in this embodiment of the pattern 374 are expansionary, in that the cross-sectional area of each projection 376 increases along its length away from the bone-facing surface 324. Consequently, the space between adjacent projections 376 decreases away from the bone-facing surface 324. A plurality of ingrowth passageways 378 are defined between the spaced-apart projections 376. The ingrowth passageways 378 receive therein living bone tissue from the medial plateau against which the bone-facing surface 324 is applied, thereby encouraging osseointegration with the implant 320. The expansionary projections 376 therefore define ingrowth passageways that are wider closer to the bone-facing surface 324, and narrower further away from the bone-facing surface 324. The ingrowth passageways 378 intersect one another to form a grid-like arrangement. Such a configuration of the pattern 374 can be suitable, for example, where it is desired to encourage the grid-like ingrowth of living bone tissue over a significant portion of the bone-facing surface 324.

FIG. 26C shows another pattern 374 having multiple projections 376 on the bone-facing surface 324. The bone-facing surface 324 in FIG. 26C has a recessed portion 380 from which the projections 376 extend. As with the projections 376 of FIG. 3A, the projections 376 in this embodiment of the pattern 374 are expansionary. Consequently, the space between adjacent projections 376 decreases away from the surface of the recessed portion 380, and the ingrowth passageways 378 are therefore wider closer to the surface of the recessed portion 380, and narrower further away from the surface of the recessed portion 380. The ingrowth passageways 378 are also disposed in a grid-like arrangement. Such a configuration of the pattern 374 can be suitable where it is desired to encourage the grid-like ingrowth of living bone tissue over a significant portion of the bone-facing surface 324 and within the recessed portion 380. The osseointegration can therefore occur deeper within the body 322 of the implant 320, which can provide for a more secure attachment of the implant 320 to the bone tissue.

FIG. 26D shows another pattern 374 having multiple projections 376 on the bone-facing surface 324. The projections 376 in this embodiment of the pattern 374 are tapered, in that the cross-sectional area of each projection 376 decreases along its length away from the bone-facing surface 324. Consequently, the space between adjacent projections 376 increases away from the bone-facing surface 324. The ingrowth passageways 378 are therefore narrower closer to the bone-facing surface 324, and wider further away from the bone-facing surface 324. The ingrowth passageways 378 are disposed in a grid-like arrangement as well. Such a configuration of the pattern 374 can be suitable, for example, where it is desired to encourage the grid-like ingrowth of living bone tissue over a significant portion of the bone-facing surface 324, and where it is desired that the living bone tissue within the ingrowth passageways 378 expand in thickness away from the bone-facing surface 324.

In light of the preceding, it will be appreciated that many different configurations of the pattern 374 are within the scope of the present disclosure, and can be employed with the implant 320, for example, depending on the bone tissue being replaced, the desired extent of osseointegration, and amount of time available for osseointegration.

Figure 30:
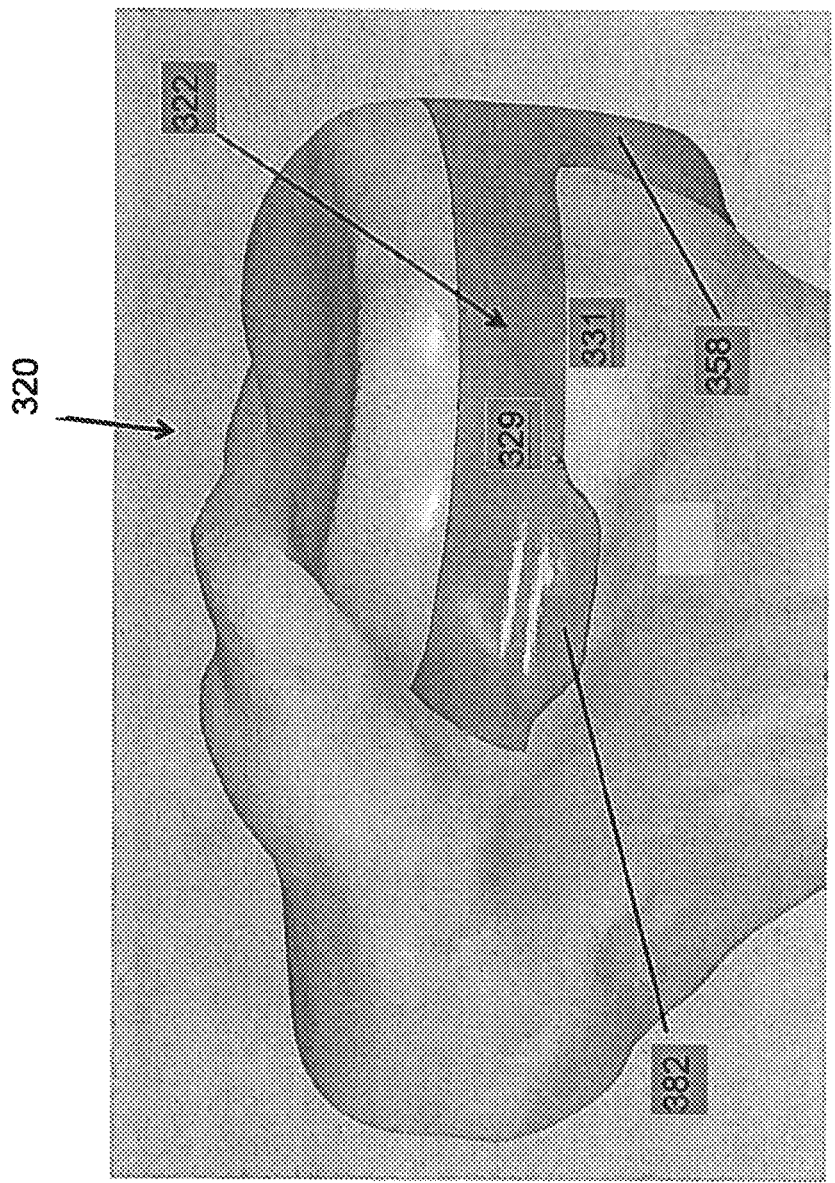
FIG. 30 is a front perspective view of the base plate of the tibial orthopedic implant shown in FIG. 25, implanted on the partially resected medial bone surface of the proximal tibia, according to an embodiment where the base plate includes a retaining rim and shown with an articulation plate connected thereto.

Now referring to FIG. 30, in an embodiment, the body 322 can also have a retaining rim 382. The retaining rim 382 helps to secure the body 322, and thus the implant 320, to the tibia T, for example in embodiments where the flange 358 covers only a portion of the periphery of the transverse planar section outside of the medial wall. As can be seen, the retaining rim 382 abuts against the first retaining surface 331 (outer surface) of the tibia T adjacent to the edge of the medial plateau (resected portion) thereof. In so doing, the retaining rim 382 overlaps the edge, and substantially reduces or prevents the movement of the implant 320 relative to the medial plateau of the tibia T. The retaining rim 382 can be any member extending longitudinally along the Tibia T as a continuous segment along a portion, or all, of the length of the first retaining surface 331. The retaining rim 382 can extend along the entire first retaining surface 331 all the way to the flange 358. The retaining rim 382 may be raised and thus extend away from the bone-facing surface (not shown) of the body 322. This distance can be constant along the length of the retaining rim 382, or can vary to better contour the first retaining surface 331 of the tibia T against which it abuts.

In the embodiments where the body 322 is semicircular, the retaining rim 382 can be an arcuate segment. In an embodiment, the retaining rim 382 can correspond to a profile of the first retaining surface 331 of the bone tissue against which it abuts, at a location adjacent to, and below, an edge of the medial plateau 354. This profile can also be arcuate-shaped.

In the embodiment shown, the tibial orthopedic implant 320 can be anchored to the tibia T using at least one screw (or attachment device), insertable in apertures 372 defined in the flange 358, to secure the base plate 340 and, more particularly, the flange 358 onto the corresponding bone surface, transversely through the flange 358. One skilled in the art will understand that the use of an attachment device, such as the at least one screw, applied to the side of the bone surface, rather than through the top of the bone surface, avoids having to secure the prosthesis to bone tissue which can be damaged or unsuitable for such use. It is appreciated that the number and the shape of the apertures 372 can vary from the embodiment shown. For instance, the implant 320 can include one or more apertures 372.

Similarly to the above described femoral implants 20, 120, the articulating surfaces of the tibial orthopedic implants 220, 320 are also designed to be patient specific. They can be designed to compensate for deficiencies, as described above and as will be described in more details below. The shape of the articulating surfaces of the articulation plates can be designed to reproduce the outer shape of the cartilage of the proximal tibia T, which is superposed to the bone, when imaging is carried out or be an offset of the outer surface of the proximal tibia T. Similarly to the above described embodiments, if part of the cartilage covering the bone is missing or broken, when the imaging of the body structure of the patient is carried out, the articulating surface can be designed to compensate or correct the missing cartilage portion. Once again, the shape of the articulating surface can also be adjusted to correct defaults, for example in the mechanical axis of the patient's leg.

It will be understood, that when a correction of a default is desired, such a correction can be implemented either by a correction of the articulating surface 26, 126 of the femoral orthopedic implant 20, 120, by the modification of the articulating surface 226 of the tibial orthopedic implant 220, 320 or by a combined modification of the articulating surfaces 26, 126, 226 of the femoral orthopedic implant 20, 120, and the tibial orthopedic implant 220, 320. In the latter case, the desired correction is shared between the articulating surfaces 26, 126, 226 of the femoral orthopedic implant 20, 120 and the tibial orthopedic implant 220, 320 to reach the overall desired correction.

In an embodiment, the tibial orthopedic implant 220 can be anchored to the tibia T using at least one screw for securing the flange 258 onto the corresponding bone surface. In an alternative embodiment, to anchor the tibial orthopedic implant 220, 320, bone cement between the bone facing surface 224, 324 and the tibia T can also be used. In another alternative embodiment, osseointegration can also be used to anchor the tibial orthopedic implant 220, 320.

In order to conceive and implant the tibial orthopedic implant 220, 320, an imaging step of the patient's body structure is first carried out and a three-dimensional image reconstruction of the patient's body structure is performed.

A projected resection of the proximal tibia of the patient is determined based on the model obtained by the image reconstruction. The tibial orthopedic implant 220, 320 is subsequently designed and conceived with the flange 258, 358 having an internal surface 260, 360 matching the shape of the patient's unresected bone and the transverse planar section 250, 350 and the sagittal planar section 252, 352 corresponding to the projected resected sections of the proximal tibia. The articulating surface 226 is also designed to be patient specific and can compensate for deficiencies or defaults, as described above.

Therefore, before the implantation can be performed, the proximal tibia T must be resected according to the projected resection in order to be prepared to receive the tibial orthopedic implant 220, 320. The design of the present tibial orthopedic implant 220, 320 allows the resection to occur without having to cut the anterior cruciate ligaments. The resection can be performed using known resection methods and tools to perform the projected resection, and should result in the medial plateau 254, 354 and medial wall 256, 356 precisely matching the transverse planar section 250, 350 and the sagittal planar section 252, 352 of the orthopedic implant 220, 320 to be implanted.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention can be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A tibial orthopedic implant for implantation onto a proximal tibia of a patient's knee joint, the proximal tibia having a longitudinal axis, a bone surface with a resected bone section including a medial plateau and a medial wall extending upwardly from the medial plateau, the tibial orthopedic implant comprising a body having a bone-facing surface including a transverse section superposable to the medial plateau and extending substantially normal to the longitudinal axis of the proximal tibia and a sagittal section engageable with the medial wall with an acute angle being defined between the transverse section and the saggital section to provide a vertical substantial retention of the tibial orthopedic implant on the proximal tibia.

2. The tibial orthopedic implant of claim 1, wherein the acute angle between the transverse section and the sagittal section ranges between about 75 degrees to about 89 degrees.

3. The tibial orthopedic implant of claim 1, wherein at least one of the transverse section and the sagittal section is substantially planar.

4. The tibial orthopedic implant of claim 1, wherein the body further comprises at least one fixation peg protruding downwardly from the transverse section.

5. The tibial orthopedic implant of claim 1, wherein the bone-facing surface of the transverse section comprises a generally flat profile with a 3D pattern protruding therefrom.

6. The tibial orthopedic implant of claim 5, wherein the 3D pattern comprises expansionary projections defining ingrowth passageways inbetween.

7. A tibial orthopedic implant for implantation onto a proximal tibia of a patient's knee joint, the proximal tibia having a bone surface with a resected bone section including a medial plateau and a medial wall extending upwardly from the medial plateau, and an unresected side surface extending downwardly from the medial plateau, the tibial orthopedic implant comprising a body having a bone-facing surface including a transverse section superposable to the medial plateau, a sagittal section engageable with the medial wall, and a substantially U-shaped flange and a retaining rim, spaced-apart circumferentially from the U-shaped flange, the U-shaped flange and the retaining rim extending downwardly and inwardly from the transverse section and engageable with the unresected side surface of the proximal tibia and substantially conforming thereto.

8. The tibial orthopedic implant of claim 7, wherein the unresected side surface of the proximal tibia is cartilage free and the U-shaped flange and the retaining rim substantially conform the unresected and cartilage free side surface of the proximal tibia.

9. The tibial orthopedic implant of claim 7, wherein at least one of the transverse section and the sagittal section is substantially planar.

10. The tibial orthopedic implant of claim 7, wherein the body further comprises at least one fixation peg protruding downwardly from the transverse section.

11. The tibial orthopedic implant of claim 7, wherein the bone-facing surface of the transverse section comprises a substantially flat profile with a 3D pattern protruding therefrom.

12. The tibial orthopedic implant of claim 11, wherein the 3D pattern comprises expansionary projections defining ingrowth passageways inbetween.

13. The tibial orthopedic implant of claim 7, wherein the substantially U-shaped flange comprises at least one screw-receiving aperture extending therethrough.

14. The tibial orthopedic implant of claim 7, wherein the retaining rim is free of screw-receiving aperture.

15. A tibial orthopedic implant for implantation onto a proximal tibia of a patient's knee joint and including an unresected and cartilage-free side surface extending downwardly from the medial plateau, the proximal tibia having a bone surface with a resected bone section including a medial plateau and a medial wall extending upwardly from the medial plateau, the tibial orthopedic implant comprising a body having a bone-facing surface including a transverse section superposable to the medial plateau and a sagittal section engageable with the medial wall with an acute angle being defined between the transverse section and the saggital section to provide a vertical substantial retention of the tibial orthopedic implant on the proximal tibia and wherein the body of the tibial orthopedic implant further comprises a flange extending downwardly and inwardly from the transverse section and engageable with the unresected and cartilage-free side surface of the proximal tibia and substantially conforming thereto.

16. The tibial orthopedic implant of claim 15, wherein the flange is substantially U-shaped.

17. The tibial orthopedic implant of claim 15, wherein the body further comprises a retaining rim extending downwardly and inwardly from the transverse section and engageable with the unresected and cartilage-free side surface of the proximal tibia and substantially conforming thereto, the retaining rim being circumferentially spaced-apart from the flange.

18. The tibial orthopedic implant of claim 15, wherein the flange comprises at least one screw-receiving aperture extending therethrough.

19. The tibial orthopedic implant of claim 15, wherein the flange comprises at least one screw-receiving aperture extending therethrough and the retaining rim is free of screw-receiving aperture.

* * * * *